US012763198B2

(12) United States Patent
Kinnunen

(10) Patent No.: US 12,763,198 B2
(45) Date of Patent: Oct. 13, 2026

(54) AUTOMATIC SLEEP STAGING CLASSIFICATION WITH CIRCADIAN RHYTHM ADJUSTMENT

(71) Applicant: Oura Health Oy, Oulu (FI)

(72) Inventor: Hannu Kinnunen, Oulu (FI)

(73) Assignee: Oura Health Oy, Oulu (FI)

( * ) Notice: Subject to any disclaimer, the term of this patent is extended or adjusted under 35 U.S.C. 154(b) by 178 days.

(21) Appl. No.: 17/733,864

(22) Filed: Apr. 29, 2022

(65) Prior Publication Data

US 2022/0375591 A1 Nov. 24, 2022

Related U.S. Application Data

(60) Provisional application No. 63/191,735, filed on May 21, 2021.

(51) Int. Cl.
*G16H 40/63* (2018.01)

(52) U.S. Cl.
CPC .................................. *G16H 40/63* (2018.01)

(58) Field of Classification Search
None
See application file for complete search history.

(56) References Cited

U.S. PATENT DOCUMENTS

| | | | | |
|---|---|---|---|---|
| 9,968,293 | B1 | 5/2018 | Kahn et al. | |
| 10,325,514 | B2 * | 6/2019 | Arnold | A61B 5/4815 |
| 10,582,890 | B2 * | 3/2020 | Bandyopadhyay | A61B 5/4815 |
| 11,446,465 | B2 * | 9/2022 | Luo | G16H 40/67 |
| 11,510,619 | B2 * | 11/2022 | Bhagat | A61B 5/14552 |

(Continued)

FOREIGN PATENT DOCUMENTS

| | | |
|---|---|---|
| JP | 2006-325766 A | 12/2006 |
| JP | 2011-067241 A | 4/2011 |

(Continued)

OTHER PUBLICATIONS

International Search Report and Written Opinion—PCT/US2022/028556—ISA/EPO—Aug. 25, 2022.

(Continued)

*Primary Examiner* — Mamon Obeid
*Assistant Examiner* — Ashley Elizabeth Evans
(74) *Attorney, Agent, or Firm* — ARENTFOX SCHIFF LLP

(57) ABSTRACT

Methods, systems, and devices for sleep staging algorithms are described. A system may receive physiological data associated with a user from a wearable device, where the physiological data may be collected via the wearable device throughout a time interval. The system may identify a circadian rhythm adjustment model configured to weight the physiological data based on a circadian rhythm associated with the user. The system may input the physiological data and the circadian rhythm adjustment model into a machine learning classifier, and classify the physiological data, using the machine learning classifier, into at least one sleep stage of a set of sleep stages for at least a portion of the time interval, where the classifying is based on the circadian rhythm adjustment model. A graphical user interface (GUI) of a user device may display an indication of the at least one sleep stage based on classifying the physiological data.

20 Claims, 12 Drawing Sheets

(56) References Cited

U.S. PATENT DOCUMENTS

| | | | | |
|---|---|---|---|---|
| 12,268,530 | B2 | 4/2025 | Pho et al. | |
| 2011/0230790 | A1 | 9/2011 | Kozlov | |
| 2015/0190086 | A1 | 7/2015 | Chan et al. | |
| 2016/0151012 | A1 | 6/2016 | Bozkurt et al. | |
| 2018/0042540 | A1 | 2/2018 | Kinnunen et al. | |
| 2018/0064388 | A1 | 3/2018 | Heneghan et al. | |
| 2018/0125418 | A1 | 5/2018 | Haakma et al. | |
| 2020/0215299 | A1 | 7/2020 | Myllymaki et al. | |
| 2020/0237317 | A1 | 7/2020 | Newberry et al. | |
| 2020/0397366 | A1 | 12/2020 | Guazzi et al. | |
| 2022/0031233 | A1 | 2/2022 | Han et al. | |
| 2022/0265208 | A1* | 8/2022 | Heneghan | A61B 5/4812 |
| 2022/0375590 | A1 | 11/2022 | Kinnunen et al. | |

FOREIGN PATENT DOCUMENTS

| | | | |
|---|---|---|---|
| JP | 2013-056082 | A | 3/2013 |
| JP | 2013-081708 | A | 5/2013 |
| JP | 2013-116210 | A | 6/2013 |
| JP | 2013-180031 | A | 9/2013 |
| JP | 2015-532855 | A | 11/2015 |
| JP | 2017-169884 | A | 9/2017 |
| JP | 2018-186683 | A | 11/2018 |
| JP | 2020-515313 | A | 5/2020 |
| JP | 2020-156603 | A | 10/2020 |
| JP | 2022-055629 | A | 4/2022 |
| WO | 2017/143179 | A1 | 8/2017 |
| WO | 2019/012742 | A1 | 1/2019 |
| WO | 2019/160939 | A2 | 8/2019 |
| WO | 2019/168474 | A1 | 9/2019 |

OTHER PUBLICATIONS

International Search Report and Written Opinion—PCT/US2022/028552—ISA/EPO—Jul. 27, 2022.

Xin Zhang et al: “Sleep Stage Classification Based on Multi-level Feature Learning and Recurrent Neural Networks via Wearable Device”, arxiv.org, Cornell University Library, 201 Olin Library Cornell University Ithaca, NY 14853; Nov. 2, 2017 (Nov. 2, 2017, XP081284426.

Office Action received for Japanese Patent Application No. 2024-503920, mailed on Jan. 27, 2026, 28 pages (14 pages of English Translation and 14 pages of Original Document).

Office Action received for Japanese Patent Application No. 2024-503951, mailed on May 26, 2026, 15 pages (8 pages of English Translation and 7 pages of Original Document).

* cited by examiner

AUTOMATIC SLEEP STAGING CLASSIFICATION WITH CIRCADIAN RHYTHM ADJUSTMENT

CROSS REFERENCE

The present application for patent claims the benefit of U.S. Provisional Patent Application No. 63/191,735 by Kinnunen et al., entitled "AUTOMATIC SLEEP STAGING CLASSIFICATION WITH CIRCADIAN RHYTHM ADJUSTMENT," filed May 21, 2021, assigned to the assignee hereof, and expressly incorporated by reference herein.

FIELD OF TECHNOLOGY

The following relates generally to wearable devices and data processing, and more specifically to techniques for automatic sleep stage classification with circadian rhythm adjustment.

BACKGROUND

Some wearable devices may be configured to collect data from users associated with movement and other activities. For example, some wearable devices may be configured to detect when a user is asleep, and classify different sleep stages for a user. However, conventional sleep detection and classification techniques implemented by some wearable devices are deficient.

DETAILED DESCRIPTION

Figure 1:
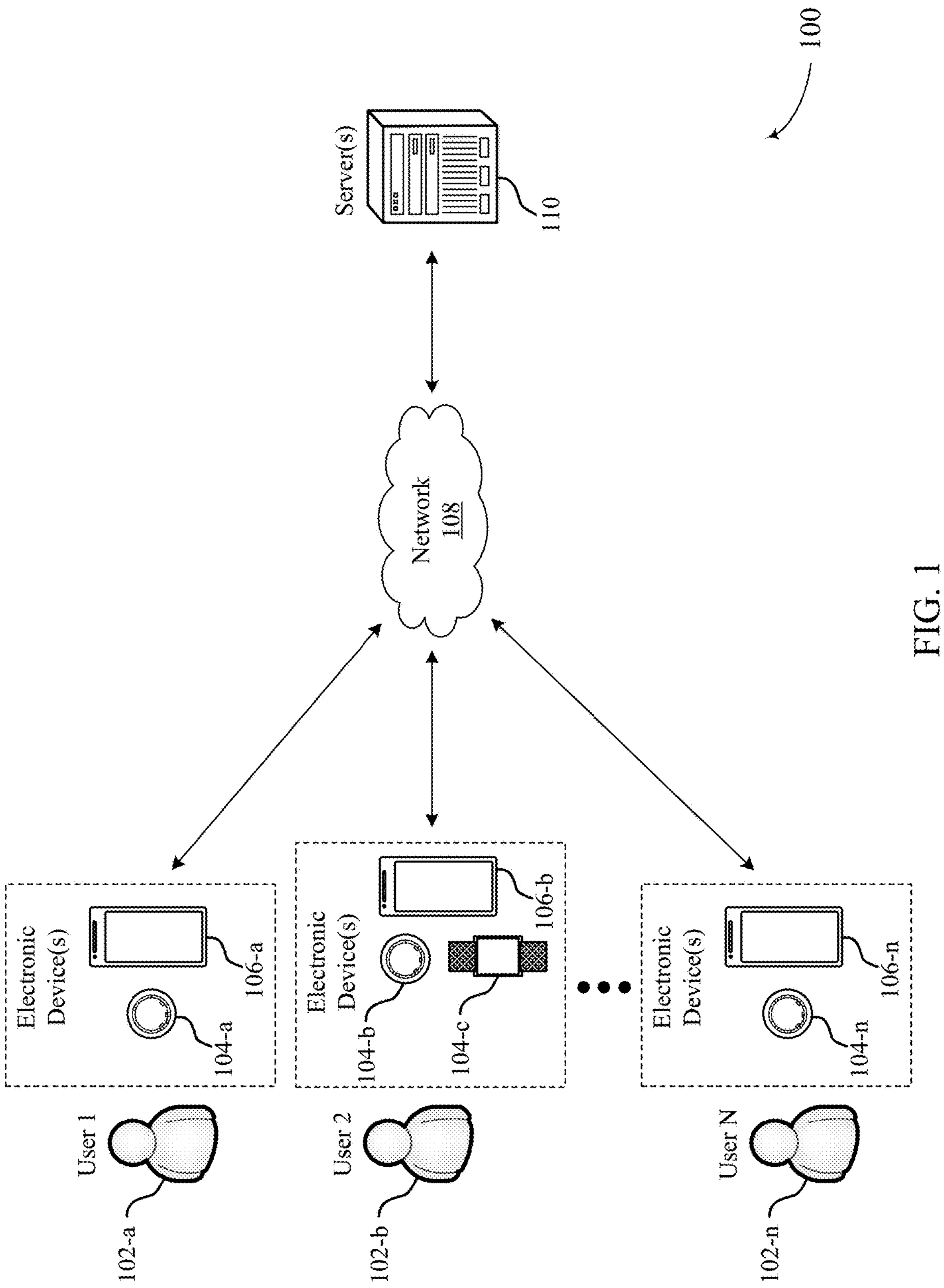
FIG. 1 illustrates an example of a system that supports sleep staging algorithms with circadian rhythm adjustment in accordance with aspects of the present disclosure.

Some wearable devices may be configured to collect data from users associated with movement and other activities. For example, some wearable devices may be configured to detect when a user is asleep. In order to efficiently and accurately track a user's sleep patterns, a wearable device may be configured to collect sleep data throughout a 24-hour period, including at night and during the daytime. Moreover, wearable devices may be configured to classify different sleep stages for a user.

Aspects of the present disclosure are directed to techniques for automatically classifying sleep stages for a user. For example, a system may receive physiological data (e.g., temperature data, heart rate data, heart rate variability (HRV) data, respiratory rate data) collected by a wearable device worn by a user, and may determine periods of time the user is asleep. Additionally, the system may automatically classify periods of time the user was asleep into one or more sleep stages. Sleep stages may include an awake sleep stage, a light sleep stage, a rapid eye movement (REM) sleep stage, a deep sleep stage, and the like. In this regard, the system may utilize data collected from the wearable device to determine periods of time the user was awake, or engaged in light, REM, or deep sleep.

In some aspects, the classified sleep stages may be displayed to a user via a graphical user interface (GUI) of a user device. In particular, a GUI may display a time interval the user was asleep, where segments of the time interval are labeled or otherwise indicated with the corresponding sleep stages. In some implementations, sleep stage classification techniques described herein may be used to provide feedback to a user regarding the user's sleeping patterns, such as recommended bedtimes, recommended wake-up times, and the like.

In some implementations, the system may utilize a machine learning classifier to classify sleep stages for a user. As such, physiological data collected from the wearable device may be input into a machine learning classifier, where the machine learning classifier is configured to classify the physiological data into one or more sleep stages throughout a given time interval. Moreover, the machine learning classifier may be configured to identify one or more features associated with the physiological data (e.g., rate of change of a parameter, minimum/maximum/average value of a parameter, a pattern between parameters), and may be configured to perform the sleep stage classification based on the identified features. In some cases, the physiological data may be normalized prior to being input into the machine learning classifier. In some cases, the machine learning classifier may be configured to tailor sleep staging algorithms to each individual user. In other words, the system may train a machine learning classifier with sleep data collected for each individual user such that the machine learning classifier is customized to perform sleep stage classification for the respective user.

Some aspects of the present disclosure may utilize circadian rhythm-derived features to further improve sleep stage classification. The term circadian rhythm may refer to a natural, internal process that regulates an individual's sleep-wake cycle, that repeats approximately every 24 hours. In this regard, techniques described herein may utilize circadian rhythm adjustment models to improve sleep stage classification. For example, a circadian rhythm adjustment model may be input into a machine learning classifier along with physiological data collected from a user via a wearable device. In this example, the circadian rhythm adjustment model may be configured to "weight," or adjust, physiological data collected throughout a user's sleep to provide more accurate sleep stage classification. In some implementations, the system may initially start with a "baseline" circadian rhythm adjustment model, and may modify the baseline model using physiological data collected from each user to generate tailored, individualized circadian rhythm adjustment models specific to each respective user.

Aspects of the disclosure are initially described in the context of wireless communications systems. Additional aspects of the disclosure are described in the context of data acquisition diagrams, a circadian rhythm adjustment model, and GUIs. Aspects of the disclosure are further illustrated by and described with reference to apparatus diagrams, system diagrams, and flowcharts that relate to sleep staging algorithms with circadian rhythm adjustment.

FIG. 1 illustrates an example of a system 100 that supports sleep staging algorithms in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, where some of the multiple electronic devices may measure physiological parameters and some may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the respective devices of the system 100 may support techniques for automatic sleep stage classification based on data collected by a wearable device. In particular, the system 100 illustrated in FIG. 1 may support techniques for detecting periods of time a user 102 is asleep, and classifying periods of time the user 102 is asleep into one or more sleep stages. For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time the user 102-*a* is (or was) asleep. Moreover, the machine learning classifier may be configured to classify periods of time into different sleep stages, including an awake sleep stage, an REM sleep stage, a light sleep stage (non-REM (NREM)), and a deep sleep stage (NREM).

In some aspects, the classified sleep stages may be displayed to the user 102-*a* via a GUI of the user device 106-*a*. In particular, a GUI may display a time interval the user 102-*a* was asleep, where segments of the time interval are labeled or otherwise indicated with the corresponding sleep stages. In some implementations, sleep stage classification techniques described herein may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve sleep stage classification. The term circadian rhythm may refer to a natural, internal process that regulates an individual's sleep-wake cycle, and that repeats approximately every 24 hours. In this regard, techniques described herein may utilize circadian rhythm adjustment models to improve sleep stage classification. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's sleep to provide more accurate sleep stage classification. In some implementations, the system may initially start with a "baseline" circadian rhythm adjustment model, and may modify the baseline model using physiological data collected from each user 102 to generate tailored, individualized circadian rhythm adjustment models specific to each respective user 102.

Techniques described herein may provide for improved sleep stage classification using data collected by a wearable device. In particular, techniques described herein may be used to determine periods of time respective users 102 are engaged in respective sleep stages (e.g., awake sleep stage, light sleep stage, REM sleep stage, deep sleep stage), that may be used to provide more valuable sleeping pattern feedback to each respective user 102. By providing a user 102 with a more comprehensive evaluation of their sleep stages and sleeping patterns, techniques described herein may enable the user 102 to effectively adjust their sleep patterns, and to improve the sleep quality and overall health for the user 102.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
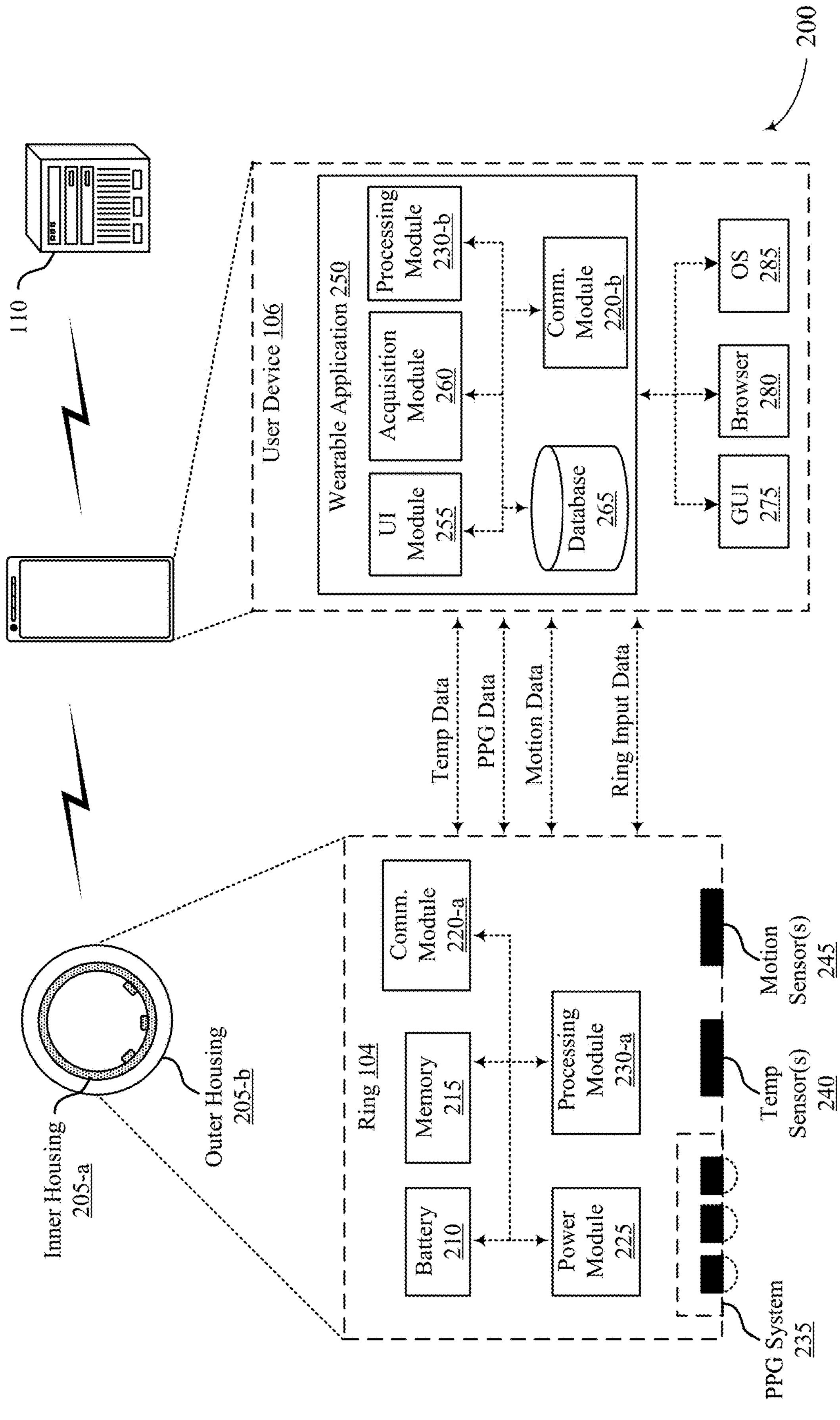
FIG. 2 illustrates an example of a system that supports sleep staging algorithms with circadian rhythm adjustment in accordance with aspects of the present disclosure.

FIG. 2 illustrates an example of a system 200 that supports sleep staging algorithms in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG)

data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205, that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a plastic/rubber band and/or tape). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate (s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*a*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, where the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, that may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ than the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform, that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during 104 a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a ring application 250, an operating system (OS), a web browser application (e.g., web browser 280), one or more additional applications, and a GUI 275. The user device 106 may further include other modules and components, including sensors, audio devices, haptic feedback devices, and the like. The ring application 250 may include an example of an application (e.g., "app") that may be installed on the user device 106. The ring application 250 may be configured to acquire data from the ring 104, store the acquired data, and process the acquired data as described herein. For example, the ring application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated on a set of contributors, including: total sleep, efficiency, restfulness, rapid eye movement (REM) sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period. Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for automatically classifying sleep stages for a user. In particular, the system 200 may support techniques for utilizing accelerometer data, PPG data, autonomic nervous system (ANS)-mediated peripheral signals, and circadian features for multi-sleep stage detection.

An increasing proportion of the public are tracking their health with wearable device technology. Sleep is one aspect of health that may be tracked using wearable devices. Part of this nightly sleep-tracking motivation is due to the recognition of sleep as essential for physical health (e.g., weight control, immune health, blood-sugar regulation), together with mental and cognitive brain health (e.g., learning, memory, concentration, productivity mood, anxiety, depression). As such, wearable devices may be used to provide a daily feedback tool guiding personal health insights and thus behavioral change that could contribute to a longer healthspan and lifespan. However, for such wearable devices to become broadly adopted by the public, the correct wearable form-factor becomes relevant, otherwise meaningful adherence is lost. This is similarly true of the utility of the type and accuracy of sensory data that such devices provide to the user, and whether that data provides meaningful, real-world insight.

Beyond adoption of sleep trackers by the general public, there is also growing interest from academic researchers and clinicians to better understand how to utilize sleep tracking data from consumer devices (e.g., wearable devices). There is a desire to understand the accuracy of sleep tracking using wearable devices relative to gold-standard measures of sleep such as PSG. Such data will aid in the appropriate levels of incorporation into research and clinical fields, and from that, large-scale healthcare management.

The gold-standard for measuring sleep is PSG, a comprehensive, multi-parameter test that is usually performed in a sleep lab. PSG typically records brain wave signals (EEG), eye movement signals (EOG), cardiac signals (ECG), muscle activity (EMG), and optionally, finger PPG. Using this combination of data, human experts or algorithms can determine the different stages of sleep (e.g., N1 (light sleep), N2 (light sleep), N3 (deep sleep), REM, and wake) across the night, a process referred to as sleep staging. According to the American Academy of Sleep Medicine (ASM), sleep staging may be done in successive segments of 30-seconds. The overall inter-scorer reliability for sleep staging has been reported to be 82-83%, with the weakest reliability found for N1, a transition stage between wakefulness and sleep. In the context of wearable devices, N1 sleep is usually combined with N2 sleep, where the combination of N1 and N2 is called light sleep to differentiate them from the deepest sleep stage, N3 sleep.

In addition to PSG, monitoring a user's sleep/activity cycles (a technique known as actigraphy) may be used for sleep-wake assessment. However, actigraphy has limitations in quantifying other features of sleep, especially sleep stages. When compared to PSG sleep assessment in healthy subjects, actigraphy may exhibit an overall sensitivity range of 72-97% and specificity range of 28-67%, Pearson's correlation coefficients for total sleep time (TST) of 0.43-0.97, sleep onset latency (SOL) of 0.64-0.82, and wake after sleep onset (WASO) of 0.36-0.39. Although actigraphy has proven to be helpful for basic wake-sleep assessment, alone, it has a limited accuracy, especially regarding the differentiation of NREM and REM sleep stages.

In contrast, when actigraphy is combined with measures of the ANS in the context of wearable devices, the accuracy of sleep quality estimations relative to PSG is equivalent to consumer EEG devices in terms of sleep-wake assessment. Field evaluation of sleep quality has improved by miniaturized sensor technology and superior mathematical modeling, especially when based on multidimensional sensor streams combining accelerometer and ANS data for 4-classes sleep stage classifications using machine learning approaches. In particular, Cohen's kappa for actigraphy alone has been reported at 0.5, while including ANS features improved results up to kappa=0.6.

Some conventional wearable devices have experienced several shortcomings in the context of sleep detection and sleep stage classification. First, a limited amount of sleep data has been collected and analyzed in a local setting using wearable devices, limiting accuracy confidence and generalizability. Second, there has been limited information concerning how different sensor data and circadian sleep models contribute to sleep quality evaluations in globally distributed data. Third, the benefit of ANS mediated peripheral signals available in wearable devices for the assessment of sleep quality has not been clearly quantified, for a number of reasons. This includes measures of the ANS from lower quality sources that are subjected to error distortion, as can happen from the wrist or arm. Fourth, while it is clear from published literature that accelerometer, ANS, temperature, and circadian rhythm-derived features are all discriminative of different physiological changes occurring during sleep, no comprehensive and systematic analysis of the relative impact of these features has been reported on a large set of individuals. Fifth, it is unclear how well some of the most complicated off-line machine learning approaches fit into real life wearable solutions, how these different approaches would perform when combining them and finally how well they generalize in global data collected from different sleep laboratories. Finally, sleep staging results from different studies are unfortunately not directly comparable due to differences in the study population, sleep staging, data quality, and data processing techniques.

Moreover, automatic sleep stage classification has historically been a challenging problem, where reference data is typically suboptimal. This is in part due to the requirement of subjective human application and interpretation of sleep staging rules used by human annotators to determine reference data eventually used for sleep stage classification. Additionally, some conventional wearable devices suffer from additional problems, often related to software updates, black box nature, and lack of independent validation. Moreover, some conventional wearable devices have been found to have limited accuracy for sleep stage classification, and tend to accurately detect only one or two of the four sleep stages (e.g., two-stage classification).

Accordingly, the system 200 may support techniques for automatic sleep staging. In particular, the components of the system 200 may be configured to determine periods of time a user is asleep, and automatically classify periods of time the user was asleep into one or more sleep stages. Sleep stages may include an awake sleep stage, a light sleep stage, a REM sleep stage, a deep sleep stage, and the like. In this regard, the system may utilize data collected from the wearable device to determine periods of time the user was awake, or engaged in light, REM, or deep sleep. The classified sleep periods may be displayed to the user via the GUI 275 of the user device 106. By providing a user with a more comprehensive evaluation of their sleep stages and sleeping patterns, techniques described herein may enable the user to effectively adjust their sleep patterns and improve the sleep quality and overall health for the user.

For example, the ring 104 may be configured to collect physiological data from a user throughout a time interval. In particular, as described previously herein, the ring 104 may collect physiological data from the user based on arterial blood flow within the user's finger. In particular, the ring 104 may utilize one or more LEDs (e.g., red LEDs, green LEDs, IR LEDs or diodes, etc.) that emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of multiple types of light sources (e.g., green LEDs, red LEDs, IR diodes) both green and red LEDs may provide several advantages over other solutions. For example, red and green LEDs have been found to have their own distinct advantages when acquiring physiological data under different conditions (e.g., light/dark, active/inactive) and via different parts of the body, and the like. For instance, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

To collect/acquire accelerometer data, the ring 104 ring may include a triaxial accelerometer that is configured to record data at some sampling frequency (e.g., 50 Hz, or some other sampling frequency). In some cases, the ring 104 and/or user device 106 may be configured to calculate standard descriptive statistics on each individual axis, after applying a 5th order Butterworth bandpass-filter between 3 to 11 Hz and taking the absolute of the filtered values. Features associated with the accelerometer data that may be acquired/collected by the ring 104, user device 106, and/or servers 110 may include trimmed mean accelerometer values (e.g., trimmed mean of accelerometer readings after removing 10% of values on maximum and minimum ends), maximum accelerometer values, minimum accelerometer values, and interquartile range (IQR) of each axis. In some cases, accelerometer data may be acquired/calculated in successive windows of 30-seconds. In some cases, the ring 104, user device 106, and/or servers 110 may calculate mean amplitude deviation (MAD) in epochs of 5-seconds from the unfiltered accelerometer data. The MAD is based on the deviation from the vector magnitude of the current 5-second epoch. For each 30-second epoch, the trimmed mean, max, and IQR accelerometer values of the MAD may be calculated. In some implementations, the ring 104 and/or user device 106 may calculate the difference in arm angle in 5-second epochs, and then aggregated in 30-seconds epochs using the trimmed mean, max, and IQR accelerometer values.

In some implementations, the ring 104 may include NTC thermistors (e.g., temperature sensors 240) configured to collect temperature data from the user. The temperature sensors 240 may be configured to collect skin temperature readings from the palm side of the user's finger base every 10 seconds, for example. Temperature data may be aggregated into epochs of 30-seconds, to be consistent with sleep staging. The ring 104, user device 106, and/or servers 110 may apply an artifact rejection step, where temperature reading values outside a plausible physiological range (e.g., values outside of 31-40 degrees Celsius, or some other range) are masked (e.g., removed, omitted, ignored). In some implementations, the ring 104 and/or the user device 106 may be configured to calculate mean (average) temperature readings, minimum temperature readings, maximum temperature readings, a standard deviation of temperature readings, and the like. Moreover, the respective temperature readings (e.g., mean, min, max, standard deviation) may be calculated for each respective epoch or other duration of time.

Regarding finger temperature, there is a clear inverse pattern with core body temperature, so that finger temperature increases across the night and decreases across the daytime. The reason is that core body temperature decreases are mechanistically accomplished through vasodilation of peripheral surface blood vessels of the skin in the extremities, particularly the hands and feet. Temporally, finger temperature precedes core body temperature by 2-3 hours, and these changes might be associated with sleep stages, making finger temperature, more so than the wrist or upper arm, particularly optimal for high accuracy sleep onset determination. Related, core body temperature follows a 24-hour rhythm, with an overall variation of 1° C. from peak to nadir. Peak temperature occurs in the evening, while the lowest point in temperature occurs at the end of the night. Indeed, sleep onset is more likely to occur when core body temperature is at its steepest rate of decline. Thereafter, core body temperature decreases during NREM sleep, and modestly increases during REM sleep.

In some implementations, in order to compute ANS-derived features such as heart rate and HRV, the ring 104, user device 106, and/or servers 110 may be configured to process raw PPG collected by the ring 104. PPG data may be collected via the PPG system 235 of the ring 104 at 125 Hz using infrared light (900 nm). Moreover, the PPG system 235 may be configured to collect PPG data only at night. To derive beat-to-beat data used to compute HRV features, a real-time moving average filter may be applied to locate local maximum and minimum values that denote the timing of each heartbeat. This procedure allows for identification of artifacts by labeling each individual interval as normal or abnormal using median filters. In particular, a deviation by more than 16 bpm from the 7-point median interval duration in its immediate vicinity may be marked as abnormal and discarded. An interval of PPG data may be included for further analysis only if five consecutive intervals values are labeled as normal (e.g., two before and two after each are acceptable intervals). Once high quality intervals have been identified, time and frequency domain HRV features may be extracted. For example, the ring 104, user device 106, and/or servers 110 may be configured to extract heart rate, rMSSD, SDNN, pNN50, frequency power in the low-frequency (LF) and high-frequency (HF) bands, the main frequency peak in the LF and HF bands, total power, normalized power, breathing rate (e.g., respiratory rate), and the like. The motivation behind these particular spectral divisions is the notion that various physiological mechanisms related to HRV manifest themselves within the boundaries of these bands. For instance, vagal activity has been found to be a major contributor to the spectral power in the HF band between 0.15 Hz and 0.4 Hz. The physiological interpretation of the spectral power in the LF band of 0.04 to 0.15 Hz is less certain, with findings attributing influences from both the sympathetic and parasympathetic branches. In some cases, the mean and coefficient of variation of the zero-crossing interval may be calculated.

Figure 3:
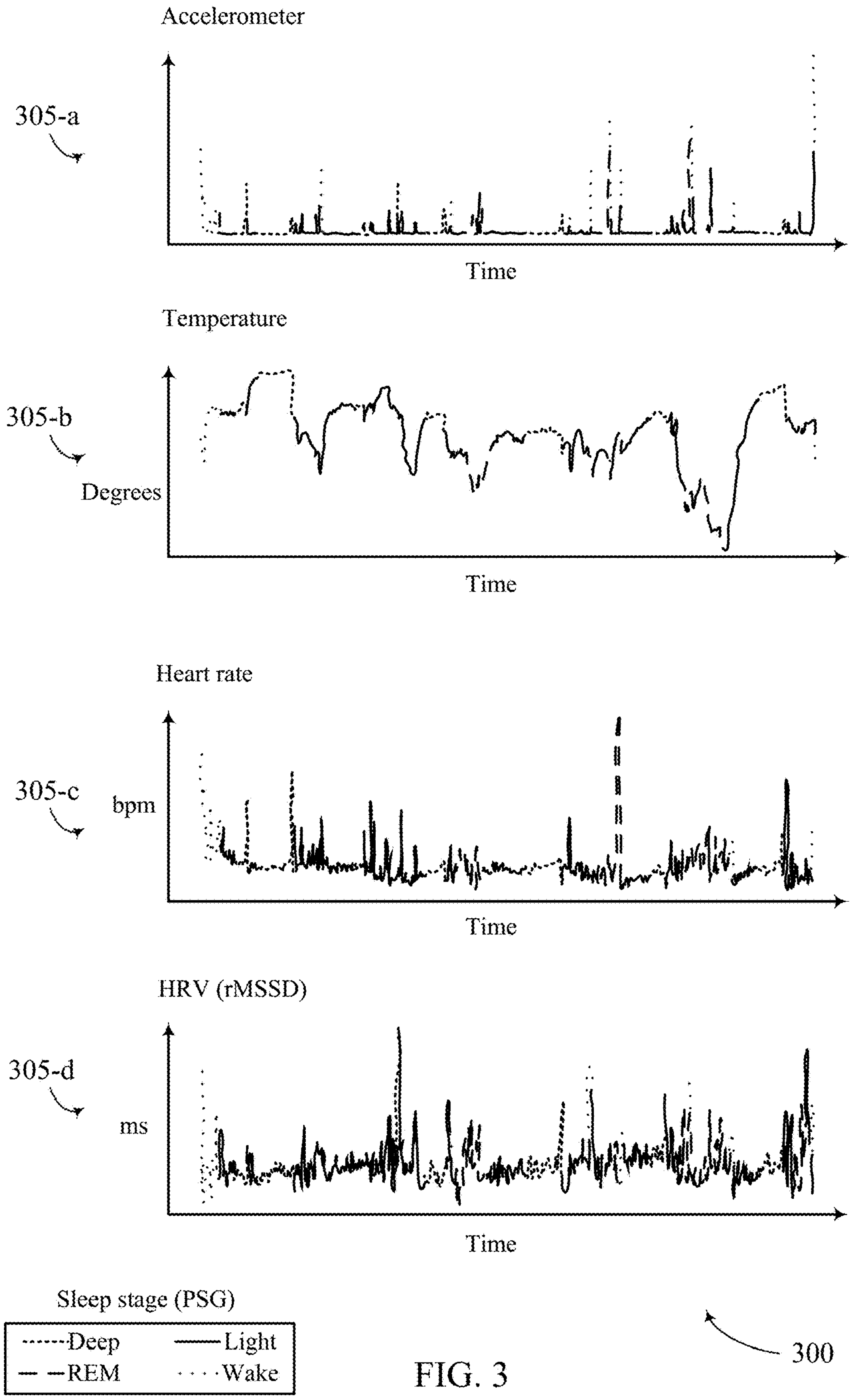
FIG. 3 illustrates an example of a data acquisition diagram that supports sleep staging algorithms with circadian rhythm adjustment in accordance with aspects of the present disclosure.

Examples of physiological data collected by a user may be further shown and described in FIG. 3.

FIG. 3 illustrates an example of a data acquisition diagram 300 that supports sleep staging algorithms with circadian rhythm adjustment in accordance with aspects of the present disclosure. In particular, the data acquisition diagram 300 includes an accelerometer data diagram 305-*a*, a temperature data diagram 305-*b*, a heart rate data diagram 305-*c*, and an HRV data diagram 305-*d*.

As may be seen in FIG. 3, the respective physiological measurements (e.g., accelerometer data, temperature data, heart rate data, HRV data) collected without a time interval may be color coded, pattern coded, or otherwise labeled as being associated with a respective sleep stage (e.g., awake sleep stage, light sleep stage, REM sleep stage, deep sleep stage). The classification of physiological data into one sleep stage of the set of sleep stages will be discussed in further detail herein.

Continuing with reference to FIG. 2, in some aspects, the ring 104, the user device 106, and/or the servers 110 may be configured to normalize the collected physiological data. For example, in some cases, the ring 104, the user device 106, and/or the servers 110 may be configured to perform one or more normalization procedures on the collected physiological data.

In some cases, physiological data (e.g., features of the physiological data) may be normalized on a per-night basis using a robust method based on the 5-95 percentiles of each of the respective parameters/features of the physiological data. Normalization may account for inter-individual differences in features (e.g., nightly heart rate or HRV). While all parameters/features (e.g., temperature data, accelerometer data, heart rate data, HRV data) may have some discriminatory power to detect different sleep stages, physiological measurements are highly individual, and absolute values can differ greatly between individuals based on parameters other than those of interest (e.g., genetics, age, etc.). Thus, performance of the sleep staging algorithms discussed herein may be improved when normalizing features of the physiological data, especially for HRV features. Feature normalization can be effective when using HRV features as the physiological principles behind using ANS activity for sleep stage classification due to the fact that there may be large differences in sympathetic and parasympathetic activity across sleep stages, and these differences can be identified within individuals as relative changes over time. In some cases, not all features/parameters of the physiological data may be normalized. For example, in some cases, accelerometer data may not be normalized, as non-normalized accelerometer data may provide information about the absolute magnitude of movement and may be useful to detect short awakenings (e.g., periods of awake sleep stages) during the night.

The physiological data may be normalized per-night using a robust z-score. In other words, the features/parameters of the physiological data (e.g., accelerometer data, temperature data, heart rate data, HRV data), may be expressed as a deviation from the night's average. Normalization may improve the accuracy of the sleep staging classification described herein, as normalization may allow the system 200 to take into account the natural variability between users and to make use of features whose absolute value is typically of very little use, given the relatively large variability between users (e.g., HRV features). Additionally, physiological data may be smoothed using a set of rolling functions in order to increase sleep staging accuracy by taking into account the past and the future at each epoch. This emulates the way that human scoring experts typically stage sleep (e.g., by constantly keeping track of what happened before the current epoch, as well as what will happen after).

In some cases, the components of the system 200 may be configured to extract features from the physiological data.

Features may be extracted offline from the available data streams (e.g., accelerometer, PPG, and temperature) using sliding windows of different lengths based on the relation between these data streams and sleep stages. For example, window lengths of 1 and 5 minutes may be used for HRV analysis to capture both short-term or faster changes in parasympathetic activity, as well as longer-term changes, as are typically present in resting heart rate. Additionally, as will be discussed in further detail herein, sensor-independent features representative of the circadian rhythm may also be identified, that have been shown to improve sleep stage classification in previous research.

In some implementations, the system 200 may calculate one or more scores (e.g., Sleep Score, Readiness Score) for the user based on the collected physiological data. The calculation of the scores may be based on the normalized physiological data. In some aspects, the one or more scores may be displayed to the user via the GUI 275 of the user device 106. In some cases, in order to reduce a latency that scores (e.g., Sleep Score, Readiness Score) are presented to the user, the scores may be calculated on the user device 106, rather than by the servers 110. Calculating the scores on the user device 106 may expedite the generation and presentation of the scores, as doing so may prevent potential network delays associated with transmitting the physiological data to the servers 110, and receiving the scores back from the servers 110.

The user device 106 may be configured to display the scores (e.g., Sleep Score, Readiness Score) and/or the physiological data collected via the ring 104. In some cases, the servers 110 may cause the user device 106 to display at least a subset of the collected physiological data and/or other data determined/identified by the system 200 to a user. For example, the user device 106 may display, via the GUI 275, raw and/or pre-processed physiological data collected by the ring 104.

In some aspects, the respective components of the system 200 may be configured to input the physiological data into a machine learning classifier. The machine learning classifier may include any machine learning classifier or algorithm known in the art including, but not limited to, a Random Forest classifier, a Naïve Bayes classifier, a deep learning classifier, an artificial neural network, and the like. Moreover, in some cases, the components may input the normalized physiological data into the machine learning classifier. In some aspects, machine learning model training and testing may be performed using a Light Gradient BoostingMachine (LightGBM) classifier, with a DART boosting and 500 estimators. LightGBM typically provides high accuracy, fast training, low memory usage, and is capable of handling missing values when data quality is too poor to calculate features.

The machine learning classifier may be trained and/or implemented by the ring 104, the user device 106, the servers 110, or any combination thereof. For example, the user device 106 may be configured to receive physiological data from the ring 104, and may transmit the physiological data to the servers 110 for classification, where the servers 110 are configured to input the physiological data into the machine learning classifier. The system 200 may be configured to perform respective processing procedures described herein at different components of the system 200 in order to reduce a latency of data presented to the user, conserve processing resources, and the like. For example, processing procedures that are more time-sensitive (e.g., lower latency requirements) and/or less computationally expensive (e.g., calculation of Sleep/Readiness Scores) may be performed via the user device 106, whereas processing procedures that are less time-sensitive and/or more computationally expensive (e.g., sleep stage classification) may be performed via the servers 110.

Subsequently, the system 200 (e.g., ring 104, user device 106, and/or servers 110) may be configured to classify the physiological data using the machine learning classifier. In particular, the system 200 may be configured to classify the physiological data into at least one sleep stage of a set of sleep stages (e.g., awake sleep stage, light sleep stage, REM sleep stage, deep sleep stage) for at least a portion of the time interval that physiological data (sleep data) was collected. That is, the system 200 may be configured to identify sleep intervals (periods of time the user was asleep) for the user, and may classify each respective sleep interval into one of an awake sleep stage, a light sleep stage, a REM sleep stage, or a deep sleep stage. In this regard, the system 200 may be configured to classify periods of light, REM, and deep sleep for the user.

In some implementations, the user device 106 may display the sleep intervals that have been classified with the corresponding sleep stages. That is, the user device 106 may display, via the GUI 275, the sleep intervals and the classified sleep stage corresponding to each respective sleep interval. This may be further shown and described with reference to FIG. 4.

Figure 4:
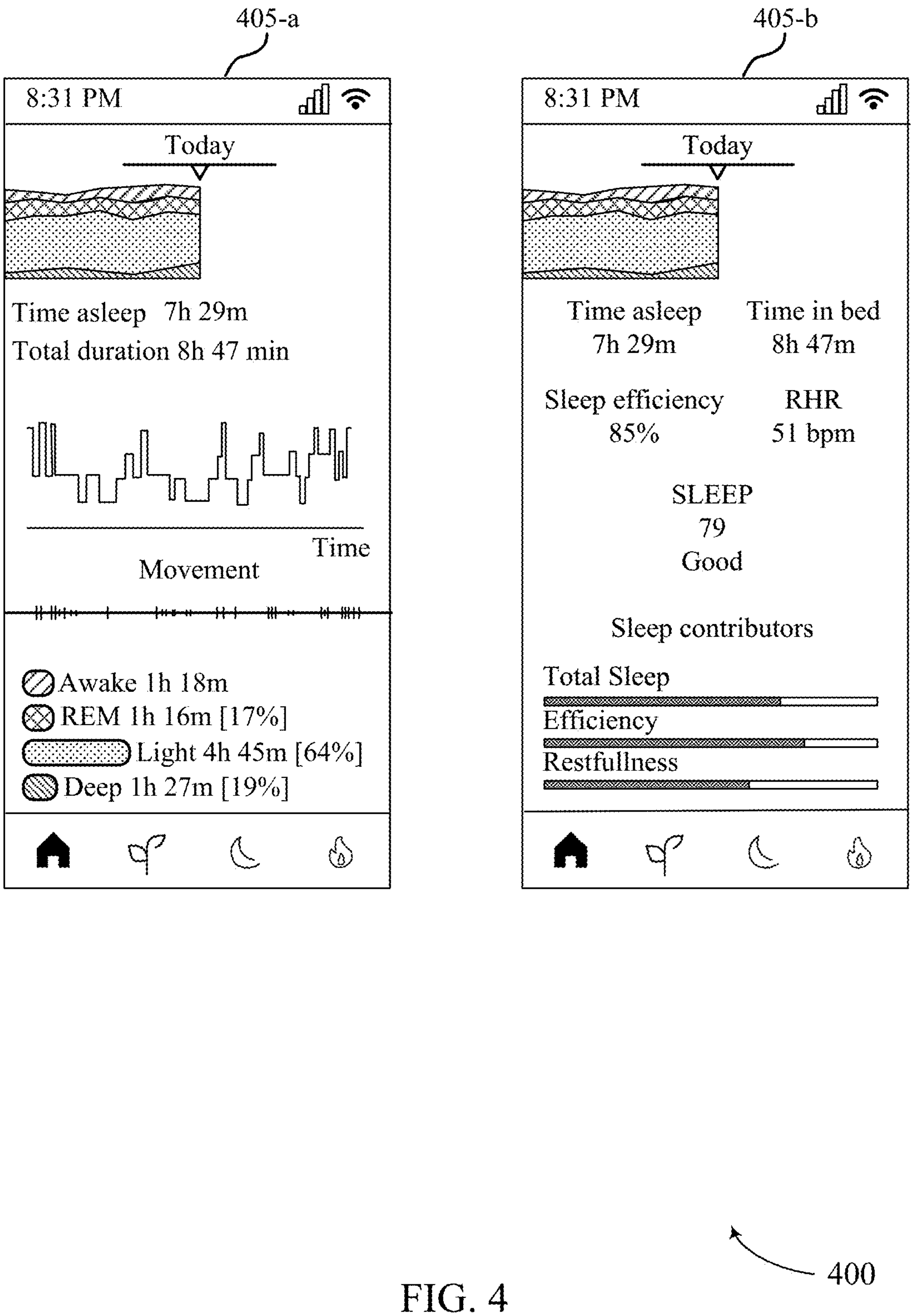
FIG. 4 illustrates an example of a graphical user interface (GUI) that supports sleep staging algorithms with circadian rhythm adjustment in accordance with aspects of the present disclosure.

FIG. 4 illustrates an example of a GUI 400 that supports sleep staging algorithms with circadian rhythm adjustment in accordance with aspects of the present disclosure. The GUI 400 illustrates several application pages 405 that may be displayed via the GUI 275 of the user device 106 illustrated in FIG. 2.

As shown in FIG. 4, an application page 405-*a* may illustrate sleep data for a user. The application page 405-*a* may display a total sleep duration for a user, a total time the user spent in bed or otherwise lying down, and the like. Additionally, application page 405-*a* may display one or more sleep intervals for the user, where each respective sleep interval is tagged, marked, or otherwise labeled with a classified sleep stage corresponding to each respective sleep interval. For example, as shown in FIG. 4, the application page 405-*a* illustrates that a user slept for a total of 7 hours and 29 minutes. This 7 hour and 29-minute time interval is displayed as a set of sleep intervals, where each sleep interval denotes a corresponding sleep stage for the respective sleep interval. In this example, sleep intervals associated with an awake sleep stage are illustrated in the top row, and sleep intervals associated with a REM sleep stage are illustrated in the second row. Further, sleep intervals associated with a light sleep stage are illustrated in the third row, and sleep intervals associated with a deep sleep stage are illustrated in the fourth (bottom) row. In some cases, the respective sleep intervals may be indicated as corresponding to different sleep stages via different colors, shading, patterns, labels, and the like. The application page 405-*a* may display total time durations for each respective sleep stage, periods of movement throughout the time interval, or both.

The application page 405-*b* may display additional data associated with the user's sleep. For example, the application page 405-*b* may display the user's calculated overall Sleep Score for the sleep day, individual contributors used to calculate the overall Sleep Score, and the like. The application page 405-*b* may be configured to display at least a subset of the physiological data collected by the ring 104 (e.g., average resting heart rate, average HRV, average temperature, and the like).

Figure 5:
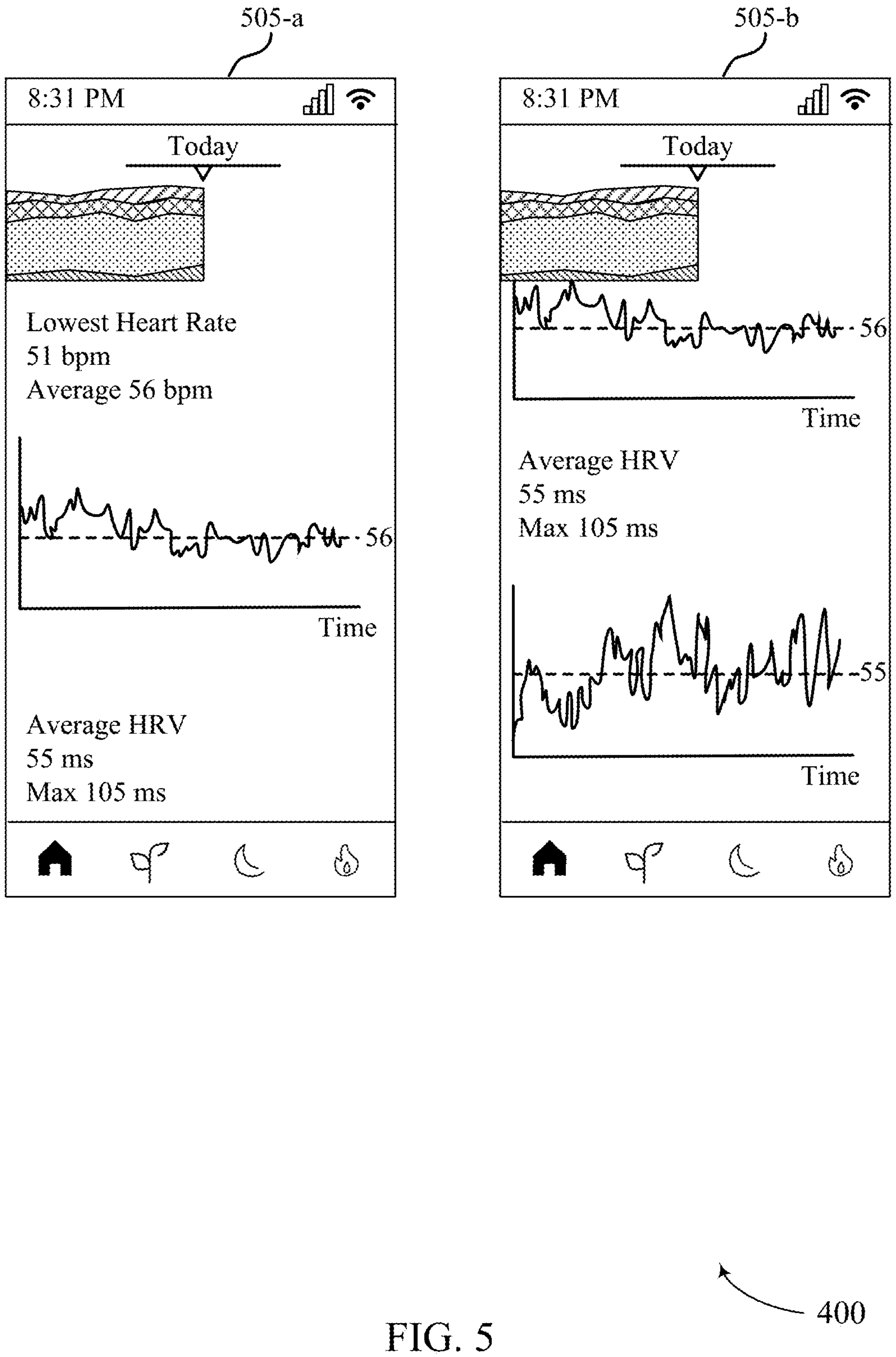
FIG. 5 illustrates an example of GUI that supports sleep staging algorithms with circadian rhythm adjustment in accordance with aspects of the present disclosure.

FIG. 5 illustrates an example of a GUI 500 that supports sleep staging algorithms with circadian rhythm adjustment in accordance with aspects of the present disclosure. The GUI 500 illustrates several application pages 505 that may be displayed via the GUI 275 of the user device 106 illustrated in FIG. 2.

The application pages 505-*a* and 505-*b* may illustrate other features/parameters associated with the collected physiological data. For example, the application page 505-*a* may illustrate the user's lowest and/or average heart rate, as well as a graph illustrating the user's changing heart rate as a function of time. Similarly, the application page 505-*b* may illustrate the user's lowest and/or average HRV, as well as a graph illustrating the user's changing HRV as a function of time.

In some implementations, the machine learning classifier may be used to identify one or more features associated with the inputted physiological data. In particular, the machine learning classifier may be configured to receive the physiological data, identify one or more features associated with the physiological data, and classify the physiological data into the corresponding sleep stages based on the identified features. The features of the physiological data may include any features known in the art, including a rate of change of the physiological data (e.g., rate of change of temperature readings, rate of change of HRV readings), a pattern between two or more parameters of the physiological data (e.g., increase in temperature along with a decrease in HRV), a maximum data value of the physiological data, a minimum data value of the physiological data, an average data value of the physiological data, a median data value of the physiological data, a comparison of a data value of the physiological data to a baseline data value for the user, or any combination thereof. Moreover, the user device 106 may be configured to display the one or more features on the GUI 274 (e.g., display the identified features on application pages 405-*a*, 405-*b*, 505-*a*, 505-*b*, or any combination thereof).

In some implementations, the system 200 may be configured to generate one or more recommendations for the user based on the collected physiological data, the classified sleep stages, the calculated Sleep/Readiness Scores, or any combination thereof. For example, in some cases, the system may identify a bed time and/or a wake time associated with the user based on classifying the physiological data into the respective sleep stages. In this regard, the system 200 may calculate a recommended bed time and/or wake time for the user that may result in improved sleep quality or overall health. The generated recommendations (e.g., bed time, wake time) may be displayed to the user via the GUI 275 of the user device 106. In some aspects, bed time determination may be performed by evaluating movement and skin temperature over time windows that extend 4 hours prior to potential go-to-bed time, 3 hours into bedtime, and 4 hours post potential wake-up time. Lack of movement and higher skin temperature may be associated with a higher probability of being in bed.

In some implementations, the system 200 may train the machine learning classifier based on inputs received from the user. For example, referring to application page 405-*a*, a user may be able to selectively adjust (via the GUI 275) a bed time and/or wake time displayed on the application page 405-*a*. For instance, if the user knows they woke up at 5:45 am instead of 5:28 am, as indicated on the application page 405-*a*, the user may be able to adjust the wake up time on the application page 405-*a* (e.g., as a user input) accordingly. In such cases, the user inputs (e.g., adjustment of the wake up time) may be input to the machine learning classifier to further train the machine learning classifier for future use.

In some aspects, the system 200 may be configured to train machine learning classifiers with physiological data collected from each respective user. In this regard, the system 200 may be configured to train (e.g., tailor) machine learning models individualized to each respective user. For example, as described previously herein, the system 200 may collect physiological data from a user during a first night of sleep (Night 1), and may classify the collected data into the respective sleep stages using the machine learning classifier. Subsequently, during a second night of sleep (Night 2), the ring 104 may collect additional physiological data from the user, and may input the additional physiological data collected during Night 2 into the machine learning classifier. In this example, the machine learning classifier may classify the additional physiological data from Night 2 into respective sleep stages based on both the physiological data from Night 1 and the additional physiological data from Night 2. This process may be repeated for n Nights, to incrementally improve the accuracy of the sleep staging by further training the machine learning classifier. In this regard, the system 200 may continually train the machine learning classifier based on data collected from the user so that the machine learning classifier becomes more efficient and reliable at classifying sleep stages for the user over time.

The machine learning classifier may be configured to use one or more parameters and/or features of the received physiological data to classify the sleep stages. For example, the machine learning classifier may utilize only accelerometer data (ACC model). In other cases, the machine learning classifier may utilize accelerometer and temperature data (ACC+T model). In other cases, the machine learning classifier may utilize accelerometer, temperature, and HRV data (ACC+T+HRV data). Additionally, or alternatively, physiological parameters/measurements may also be used by the machine learning classifier for sleep stage classification, including, but not limited to, blood oxygen level (e.g., SpO2), pulse waveforms, respiration rate, pulse oximetry, blood pressure, and the like.

For two-stage classification (e.g., classification into sleep and wake sleep stages), accelerometer-based models (e.g., ACC model) exhibited 94% accuracy (fl-score=0.67), where including temperature (e.g., ACC+T model) resulted in 95% accuracy (fl-score=0.69). Further, including HRV data (e.g., ACC+T+HRV model) led to 96% accuracy (fl-score=0.76), and including circadian features lead to a 96% accuracy (fl-score=0.78). For four-stage classification (e.g., classification into awake, light, REM, and deep sleep), accelerometer-based models (e.g., ACC model) exhibited 57% accuracy (fl-score=0.68), where including temperature (e.g., ACC+T model) resulted in 60% accuracy (fl-score=0.69). Further, including HRV data (e.g., ACC+T+HRV model) led to 76% accuracy (fl-score=0.73), and including circadian features (e.g., ACC+T+HRV+C models) lead to a 78% accuracy (fl-score=0.78).

In this regard, in some implementations, the system 200 may further utilize circadian features to classify physiological data. Mathematical modeling of the circadian rhythm may be used to account for differences in sleep stage frequency across the night. The term "circadian rhythm" may refer to a natural, internal process that regulates an individual's sleep-wake cycle, that repeats approximately every 24 hours. For example, according to human being's natural circadian rhythm, humans may generally experience a relatively higher frequency of deep sleep toward the beginning of the night, and a relatively higher frequency of REM sleep toward the latter portion of the night.

As such, by using a time elapsed during the night, time of day, and time with respect to individual circadian rhythms to formulate features, the higher relative frequency of deep sleep in the first part of the night and the higher relative frequency of REM sleep in the second part of the night can be better accounted for, leading to improved sleep stage classification accuracy. For example, in the context of two-stage classification, the inclusion of circadian features (e.g., ACC+T+HRV+C model) led to 96% accuracy (fl-score=0.78). Moreover, in four-stage classification, the inclusion of circadian features also led to a 78% accuracy (fl-score 0.78).

Accordingly, in some implementations, the system 200 may be configured to input a circadian rhythm adjustment model into the machine learning classifier, where the machine learning classifier is configured to classify the physiological data into corresponding sleep stages based on (e.g., using) the circadian rhythm adjustment model.

The circadian rhythm adjustment model may be configured to weight the physiological data based on a circadian rhythm associated with the user. In particular, the circadian rhythm adjustment model may be used to selectively "weight" probability metrics associated with given time intervals toward one sleep stage or another. In other words, the circadian rhythm adjustment model may be used to weight, or influence, whether physiological data and/or time intervals of sleep are more likely to be associated with a given sleep stage.

For example, as noted previously herein, a user may experience a relatively higher frequency of deep sleep toward the beginning of the night, and may experience a relatively higher frequency of REM sleep toward the latter portion of the night. In this regard, the circadian rhythm adjustment model may "weight" probability metrics for time periods in the beginning of the night toward a deep sleep stage, and may "weight" probability metrics for time periods in the latter portion of the night toward a REM sleep stage. In other words, the circadian rhythm adjustment model may increase the likelihood that time periods toward the beginning of the night will be classified as corresponding to a deep sleep stage, and may increase the likelihood that time periods toward the end of the night will be classified as corresponding to a REM sleep stage. In practical terms, lower resting heart rate and lower breathing rate variability (consistent breathing rhythm) are associated with deep sleep. In cases where circadian rhythm is used as part of the model, resting heart rate may be higher soon after the user's normal go-to-bed times or in the beginning of sleep period when sleep pressure is still high, and still indicate higher probability of deep sleep (contribute positively to selection of deep sleep) than at a later instance during the sleep. Similarly, in morning hours very consistent breathing rhythm can be required as an indication of deep sleep, otherwise the model will indicate light sleep or REM sleep. Below we will explain the separate roles of time with respect to: (1) circadian rhythm, (2) time with respect to prevailing sleep pressure, and (3) accumulated sleep duration (3).

In some implementations, algorithms and other machine learning classifiers may adjust themselves depending on general night-day-rhythm of human beings (e.g., circadian rhythm). In some cases, adjustment can be programmed to work in accordance to the prevailing circadian phase of an individual user. For example, adjustment may be programmed based not on the local time, but in relation to what time of the day the person usually goes to bed and/or wakes up, and/or what time of the day they normally expose themselves to physical activities and light, or according to their body temperature or hormonal or blood glucose variations that occur in about 24-hour cycles.

In some implementations, a generalized circadian rhythm adjustment model may be used for each user. In other words, data from multiple users may be used to generate a generalized circadian rhythm adjustment model that may be used to classify sleep stages for multiple users. In other cases, circadian rhythm adjustment models may be customized, or tailored, to each respective user. In particular, physiological data from each respective user may be used to generate a customized circadian rhythm adjustment model that will be used for the respective user.

For example, in some cases, the system 200 (e.g., ring 104, user device 106, servers 110) may receive or otherwise identify a baseline circadian rhythm adjustment model (e.g., generalized circadian rhythm adjustment model). In this example, the system 200 may collect physiological data from the user, and may selectively modify the baseline circadian rhythm adjustment model based on the collected physiological data in order to generate a tailored, or customized, circadian rhythm adjustment model that will be used for sleep stage classification for the respective user. In other words, the system 200 may utilize physiological data collected by the user to further modify and refine the circadian rhythm adjustment model for the user.

Since the probability of different sleep stages varies during the entire 24-hour cycle, varying probabilities of the respective sleep stages may be pre-programmed to the algorithm. Moreover, the phase of the circadian rhythm may be used as an input in the training/development of the machine learning classifier. As such, the machine learning classifier/algorithm may learn how different physiological signals respond differently to the sleep stages depending on the phase of the circadian rhythms. For example, varying breathing rate generally indicates REM sleep. In this regard, a quantity of variance in breathing rate indicative of REM sleep can be programmed to vary according to the circadian phase. The above principle can be applied to all physiological features that are used in estimation of sleep stages. Now, if a user is an early sleeper (also referred to as morningness chronotype), but occasionally goes to bed later than normal, in case of the later bedtime the algorithm can favor REM sleep earlier (relative to the start of the sleep) than it would have done in case of a normal go-to-bed time. In practice, this would be seen as earlier or longer REM sleep episodes already at the end of the first and second roughly-90-min sleep cycles (that are part of the normal sleep pattern of human beings).

Sleep is a dynamic process regulated by many internal and external factors. According to the traditional two-process model of sleep, there are two main components that determine the time when we go to sleep and the time when we wake up, as well as the overall structure and depth of our sleep: (1) the circadian rhythm, and (2) homeostatic sleep drive. The circadian rhythm promotes sleep at night and wakefulness during the daytime. This wave-like rhythm has an internal, approximate 24-hour period, that is synchronized by external timing cues such as sunlight. The homeostatic sleep drive refers to how the pressure for sleep linearly builds up in our brain during wakefulness, and decreases in an exponential manner during sleep, and especially deep NREM sleep.

Accordingly, in order to capture both the circadian rhythm and homeostatic sleep drive, the circadian rhythm adjustment model may include multiple components: (1) a circadian drive component, (2) a homeostatic sleep pressure component, and (3) and elapsed sleep duration component. These components of the circadian rhythm adjustment model may be further shown and described with reference to FIG. 6.

Figure 6:
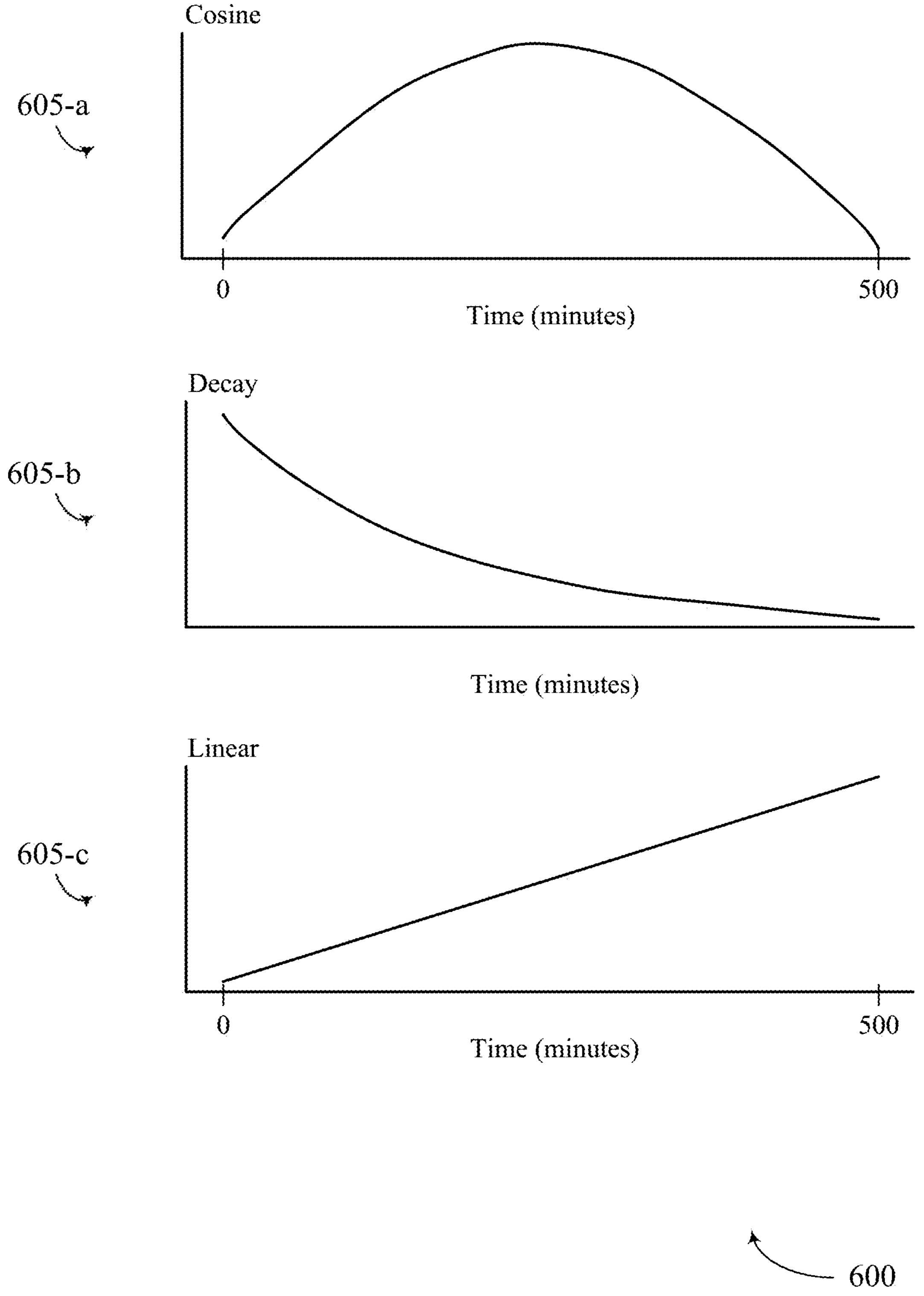
FIG. 6 illustrates an example of a circadian rhythm adjustment model that supports sleep staging algorithms with circadian rhythm adjustment in accordance with aspects of the present disclosure.

FIG. 6 illustrates an example of a circadian rhythm adjustment model 600 that supports sleep staging algorithms with circadian rhythm adjustment in accordance with aspects of the present disclosure. The circadian rhythm adjustment model 600 shown in FIG. 6 may include a circadian drive component 605-*a*, a homeostatic sleep pressure component 605-*b*, and an elapsed sleep duration component 605-*c*.

Generally, the time "0" across the graphs illustrated in FIG. 6 illustrates an expected, or calculated, bed time (e.g., go-to-bed time) for the user, or a most common bed time for each user. For example, the bed time (e.g., Time=0) may be determined based on physiological data collected for a user in the last two weeks and for sleep periods that have lasted more than three hours, preferably giving more weight to the immediately preceding nights (to account for potential circadian rhythm adjustments during the most recent days). As such, the start time for the respective components (e.g., circadian drive component 605-*a*, a homeostatic sleep pressure component 605-*b*, and an elapsed sleep duration component 605-*c*) may be adjusted over time as more physiological data is collected.

It is noted herein that the modeling of the components 605 may be based on an assumption that users go to bed at their most typical bed times (e.g., go-to-bed times), but may not always be the case. In real life, bed times may vary according to weekday/weekend days, work shifts, travel/time zone shifts, social reasons, day-time napping, and other factors. Accordingly, the components 605 may be adjusted to account for real-world variability.

As shown in FIG. 6, the circadian drive component 605-*a* may be represented as a sinusoidal function (e.g., cosine function). In this regard, the cosine function of the circadian drive component 605-*a* may start at the expected bed time for a user, and may be determined by the system based on the physiological data. In particular, the bed time for the user may be automatically detected based on low motion and/or high skin temperatures. Low motion can mean that less than 50-70% of one-minute periods in a 2-4 hour time window has any motions that would exceed a predetermined limit (such as 50-100 mg) in acceleration, for example. High skin temperature can mean that skin temperature exceeds a pre-determined limit of about 34-35° C., for example. Naturally, these features can be combined, for example, so that more motion can be allowed to mark a restful minute in case of warmer skin temperature.

Continuing with reference to the circadian drive component 605-*a*, there may be cases a user stays in bed for longer than five-hundred minutes. In such cases, the cosine function of the circadian drive component 605-*a* may either continue to the negative side (same cosine function), or it may be zero. More generally, the wavelength of the cosine function (1000 minutes in the graph for the circadian drive component 605-*a*) could be adjusted if a user typically sleeps for very short or very long periods of time. In some cases, the circadian drive component 605-*a* may be adjusted by 1000*typical sleep duration (min)/880, where typical sleep duration can be median sleep duration or some higher percentile (such as 75th percentile) representing a full night's sleep for the respective user.

Additionally, or alternatively, the user device 106 and/or server 110 may generate/model the circadian drive component 605-*a* for the user based on the user's acquired physiological data. For example, when the user wakes up in the morning and logs into the ring application 250 on the user device 106, the user device 106 and/or server 110 may use physiological data acquired from the ring 104 throughout the duration of the night and the previous day (within the same sleep day) to generate/model the circadian drive component 605-*a*. In this example, the generated circadian drive component 605-*a* for the respective night/sleep day may be used to generate/model other circadian drive components 605-*a* for subsequent nights/sleep days.

Comparatively, the homeostatic sleep pressure component 605-*b* may indicate the decay of homeostatic sleep pressure across the night, and may be represented as an exponential decay function. The homeostatic sleep pressure component 605-*b* illustrates that users typically exhibit the most sleep pressure at the beginning of the night, where the sleep pressure decays most rapidly during the first hours of sleep and are generally rich in deep NREM sleep.

In some implementations, the exponential decay function for the homeostatic sleep pressure component 605-*b* may be adjusted based on how long a user has stayed awake, or if the user accumulated sleep debt (e.g., periods of time spanning several days the user has experienced less sleep than suggested or required). One simple way of doing this adjustment may include starting the exponential decay function at a higher value in case the user has been awake longer than 16 hours, or lower if the user has been awake shorter than 16 hours. For example, the exponential decay function of the homeostatic sleep pressure component 605-*b* may start from 1.0*hours awake/16. Also, if the user has accumulated sleep debt, the exponential decay function could start higher. The length of the exponential decay function (the time when the exponential decay function reaches zero) could be adjusted based on 500*typical sleep duration (min)/440, where typical sleep duration can be median sleep duration or some higher percentile (such as 75th percentile) representing a full night's sleep for a particular user. Additionally, or alternatively, the system 200 may adjust the slope or level of exponential decay of the homeostatic sleep pressure component 605-*b*.

Accordingly, in some cases, the system 200 may identify a time duration from a most recent sleep period for the user, and may input the time duration into the machine learning classifier, where the machine learning classifier is configured to classify physiological data into corresponding sleep stages based on the time duration. In such cases, the time duration from the last sleep period may indicate an amount of sleep pressure that the user is experiencing, and may be used to adjust the homeostatic sleep pressure component 605-*b* of the circadian rhythm adjustment model.

Lastly, the elapsed sleep duration component 605-*c* represents the time elapsed since the beginning of the night, and may be represented as a linear function ranging from 0 to 1. The elapsed sleep duration component 605-*c* may take into account the well-known asymmetry of sleep stages across a typical night of sleep (e.g., more deep NREM early in the night, and more REM sleep in the latter portion of the night). This asymmetry is also covered by the exponential decay function. However, time elapsed gives additional value because human sleep also has linearly repeating patterns, such as 90-min sleep cycles and general dependency on what happened previously (e.g., one may have exceptionally high sleep pressure even after 1 hour of sleep, but sleep cycles are still modulated based on how long the user has been sleeping). As such, in some cases, both factors may be used to best characterize human sleep.

Continuing with reference to the elapsed sleep duration component 605-*c*, (accumulated time in bed/accumulated sleep thus far), time=0 may stay at the user's typical (e.g., expected) bed time in case of normal sleep pattern. However, in cases where a user stays awake only shortly after a long sleep period, the elapsed sleep duration component 605-*c* could start at a larger (e.g., non-zero) value. One way of applying this principle would be that the starting time (expected time accumulated in bed) would reduce by 1 minute with each 1 minute of staying out of bed. In practice, after a normal 8 hours of time spent in bed, when the next sleep period is evaluated, the elapsed sleep duration component 605-*c* may start from zero after about 8 hours of staying out of bed (e.g., at 3 pm assuming the user gets up at 7 am).

Physiologically, all sleep stages differ from each other with respect to typical breathing, ANS, and body movement patterns. These behavioral differences and physiological responses to sleep phases, and central nervous system and ANS coupling, provide the theoretical framework for wearable sleep assessment. When combining such data streams (e.g., physiological data) from the ring 104 with sensor-independent circadian features (e.g., circadian rhythm adjustment model) designed to better account for differences in sleep stage distribution across the night, as well as features normalization and machine learning techniques, accuracy for two-stage and four-stage sleep stage classification has been found to approach results previously reported only for EEG-based systems.

When looking at performance epoch by epoch, it may be understood how the different data streams of the physiological data contribute to model performance. In particular, accelerometer-only models (ACC models) may detect awake sleep stages, as movement alone cannot differentiate between more complex brain and sleep stages. Adding finger temperature (ACC+T models) may result in small performance improvements in the detection/classification of different sleep stages. The largest improvement for four-stage classification performance obtained when including HRV features (ACC+T+HRV models), as HRV data is more tightly coupled to brain wave changes occurring during sleep. Adding HRV features provided an improvement in accuracy from 60% to 76% in the context of four-stage classification. Notably, adding circadian features that are sensor-independent (ACC+T+HRV+C models) was found to lead to additional improvements in the detection of sleep stages, specifically deep NREM and REM sleep.

The hardware and software development of the system 200 has been found to exhibit the high sensitivity for sleep stage classification across all sleep stages, ranging from 74% to 98% accuracy. Indeed, it has been found that combining multiple sensor data streams from a user's finger via the ring 104, as well as circadian-features and feature normalization, may achieve high sensitivity and specificity for all sleep stages and wakefulness. While other studies have shown similar results for the detection of a specific stage such as deep sleep, this typically comes at the expense of the performance in detecting other sleep stages (e.g., resulting in REM or awake sleep stage sensitivity as low as 50%).

Accelerometer-only data (ACC models) improved the current state of the typical sleep and wake detection accuracy that is usually based on actigraphy and simple motion-intensity features. In particular, the use of physiological data including multiple parameters (e.g., temperature, heart rate, HRV) may better discriminate between sleep stages and are less prone to calibration error or hardware differences. This includes capturing relative deviations from previous windows or using trigonometry identities to estimate finger-derived motion in a more robust manner, as these features are less likely to be confounded by, for example, a person's partner, pet, etc. moving in bed. While results for accelerometer-only models are still below those of gold standard PSG, especially for four-stage classification, using the proposed features described herein has been found to lead to good (e.g., improved) performance in the detection/classification of sleep stages, including deep NREM sleep that consumer devices have historically struggled to accomplish, and not only wake states.

As noted previously herein, there is a clear inverse pattern with core body temperature, so that finger temperature increases across the night and decreases across the daytime, where sleep onset is more likely to occur when core body temperature is at its steepest rate of decline. However, after determination of sleep onset, it has been found that adding peripheral finger temperature measurement leads to better sleep staging accuracy. As such, finger temperature (e.g., temperature data collected by the ring 104) still represents a relevant and important sensory signal for determination of sleep onset and offset, making this unique data feature streaming important and a potentially overlooked one.

The largest improvement in sleep stage classification performance may occur when adding HRV features. The ring 104 may use optical technology to capture beat-to-beat intervals and compute heart rate or more complex HRV features to estimate sleep stages. This is due to the tighter link between central nervous system activity and changes in ANS that can be captured non-invasively using HRV features. In particular, the physiology of sleep shows consistent patterns that are specific to differences between NREM and REM sleep as well as each individual stage. For example, during REM sleep heart rate increases and shows higher variability. An improvement of 15-25% in four-stage classification can be obtained when including heart rate data. However, the additional inclusion of HRV features representative of parasympathetic activity can lead to increased performance. During NREM sleep both heart rate and HRV can progressively decrease. These patterns are consistent with increased parasympathetic activity during NREM sleep and increased sympathetic activity during REM sleep. Given the fast nature of these changes that were quantified from the finger pulse waveform, heart rate and HRV may indeed potentially reflect changes in brain waves captured by PSG.

The distribution of sleep stages across the night can change due both to idiosyncratic and expected patterns. The latter include both the typical nature of sleep cycles, with stages following a sequence during approximately 70-120 minutes cycles, as well as how the distribution of sleep stages changes throughout the night. In particular, deep NREM sleep is typically more present during the first third of the night, while REM sleep is more present during the second half of the night, when each bout of REM can also last longer. Modeling the waxing-and-waning of the circadian rhythm across the night, when sleep is the most stable, with core temperature and heart rate close to their minimum diurnal levels, as well as the decay of homeostatic sleep pressure and the time elapsed since the beginning of the night, resulted in improved accuracy up to 78%. Sleep stage detection in literature has tried to account for temporal associations between stages using various techniques, from Markov models to neural networks. However, modeling changes in sleep stage distribution across the night with sensor-independent circadian features provides a clear improvement in classification performance.

Figure 7:
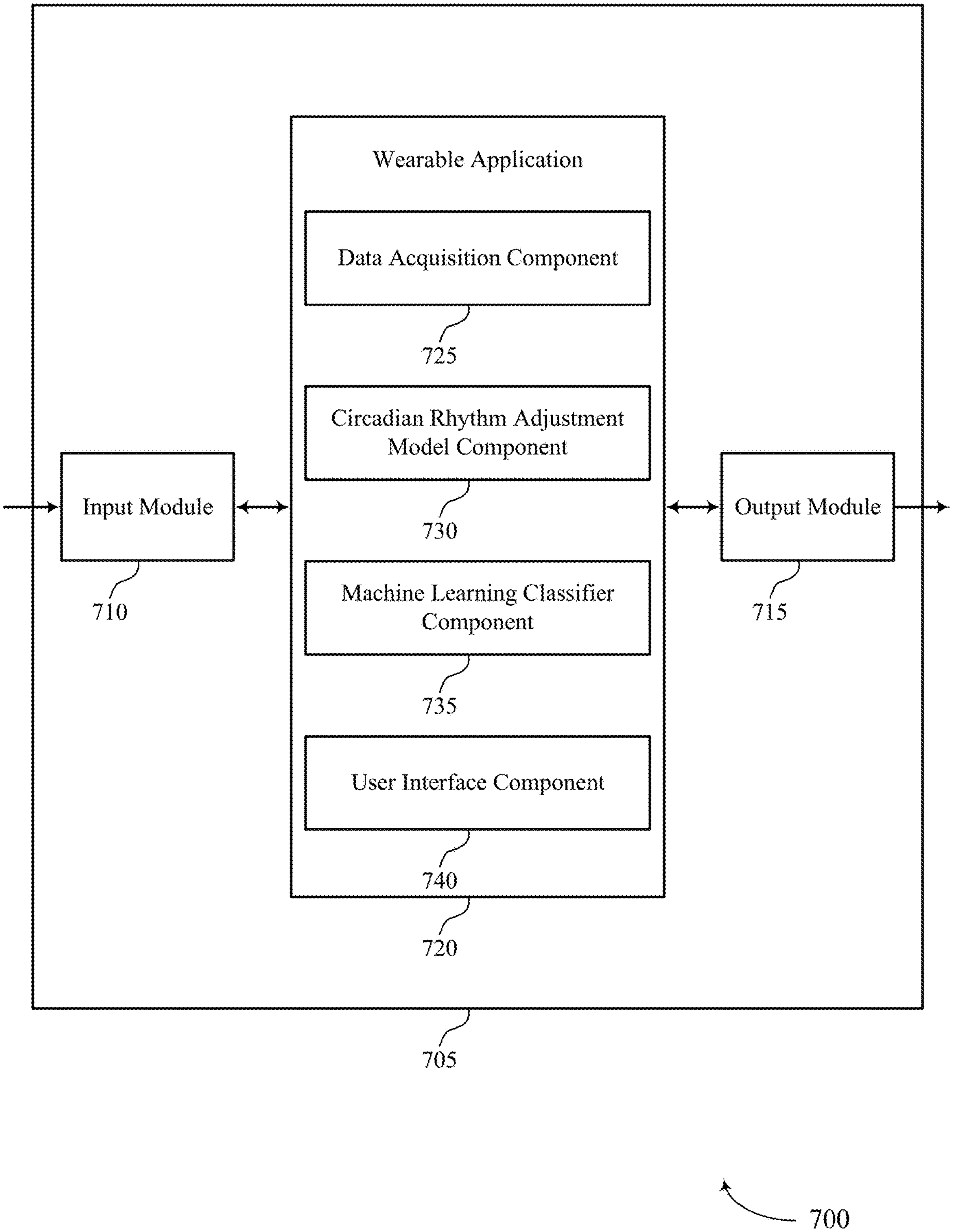
FIG. 7 shows a block diagram of an apparatus that supports sleep staging algorithms with circadian rhythm adjustment in accordance with aspects of the present disclosure.

FIG. 7 shows a block diagram 700 of a device 705 that supports sleep staging algorithms with circadian rhythm adjustment in accordance with aspects of the present disclosure. The device 705 may include an input module 710, an output module 715, and a wearable application 720. The device 705 may also include a processor. In some aspects, the device 705 may include an example of a mobile device, as illustrated in FIGS. 1 and 2. Each of these components may be in communication with one another (e.g., via one or more buses).

The input module 710 may manage input signals for the device 705. For example, the input module 710 may identify input signals based on an interaction with a wearable device (e.g., ring), modem, a keyboard, a mouse, a touchscreen, or a similar device. These input signals may be associated with user input or processing at other components or devices. In some cases, the input module 710 may utilize an operating system such as iOS®, ANDROID®, MS-DOS®, MS-WINDOWS®, OS/2®, UNIX®, LINUX®, or another known operating system to handle input signals. The input module 710 may send aspects of these input signals to other components of the device 705 for processing. For example, the input module 710 may transmit input signals to the wearable application 720 to support a method and system for supplemental sleep detection. In some cases, the input module 710 may be a component of an I/O controller 910 as described with reference to FIG. 9.

The output module 715 may manage output signals for the device 705. For example, the output module 715 may receive signals from other components of the device 705, such as the wearable application 720 or servers, and may transmit these signals to other components or devices (e.g., wearable device, servers). In some examples, the output module 715 may transmit output signals for display in a user interface, for storage in a database or data store, for further processing at a server or server cluster, or for any other processes at any number of devices or systems. In some cases, the output module 715 may be a component of an I/O controller 910 as described with reference to FIG. 9.

For example, the wearable application 720 may include a data acquisition component 725, a circadian rhythm adjustment model component 730, a machine learning classifier component 735, a user interface component 740, or any combination thereof. In some examples, the wearable application 720, or various components thereof, may be configured to perform various operations (e.g., receiving, monitoring, transmitting) using or otherwise in cooperation with the receiver 710, the transmitter 715, or both. For example, the wearable application 720 may receive information from the receiver 710, send information to the transmitter 715, or be integrated in combination with the receiver 710, the transmitter 715, or both to receive information, transmit information, or perform various other operations as described herein.

The wearable application 720 may support techniques for detecting sleep stages in accordance with examples as disclosed herein. The data acquisition component 725 may be configured as or otherwise support a means for receiving physiological data associated with a user from a wearable device, the physiological data collected via the wearable device throughout a time interval. The circadian rhythm adjustment model component 730 may be configured as or otherwise support a means for identifying a circadian rhythm adjustment model configured to weight the physiological data based at least in part on a circadian rhythm associated with the user. The machine learning classifier component 735 may be configured as or otherwise support a means for inputting the physiological data and the circadian rhythm adjustment model into a machine learning classifier. The machine learning classifier component 735 may be configured as or otherwise support a means for classifying the physiological data, using the machine learning classifier, into at least one sleep stage of a plurality of sleep stages for at least a portion of the time interval, wherein the classifying is based at least in part on the circadian rhythm adjustment model. The user interface component 740 may be configured as or otherwise support a means for causing a GUI of a user device to display an indication of the at least one sleep stage of the plurality of sleep stages based at least in part on classifying the physiological data.

Figure 8:
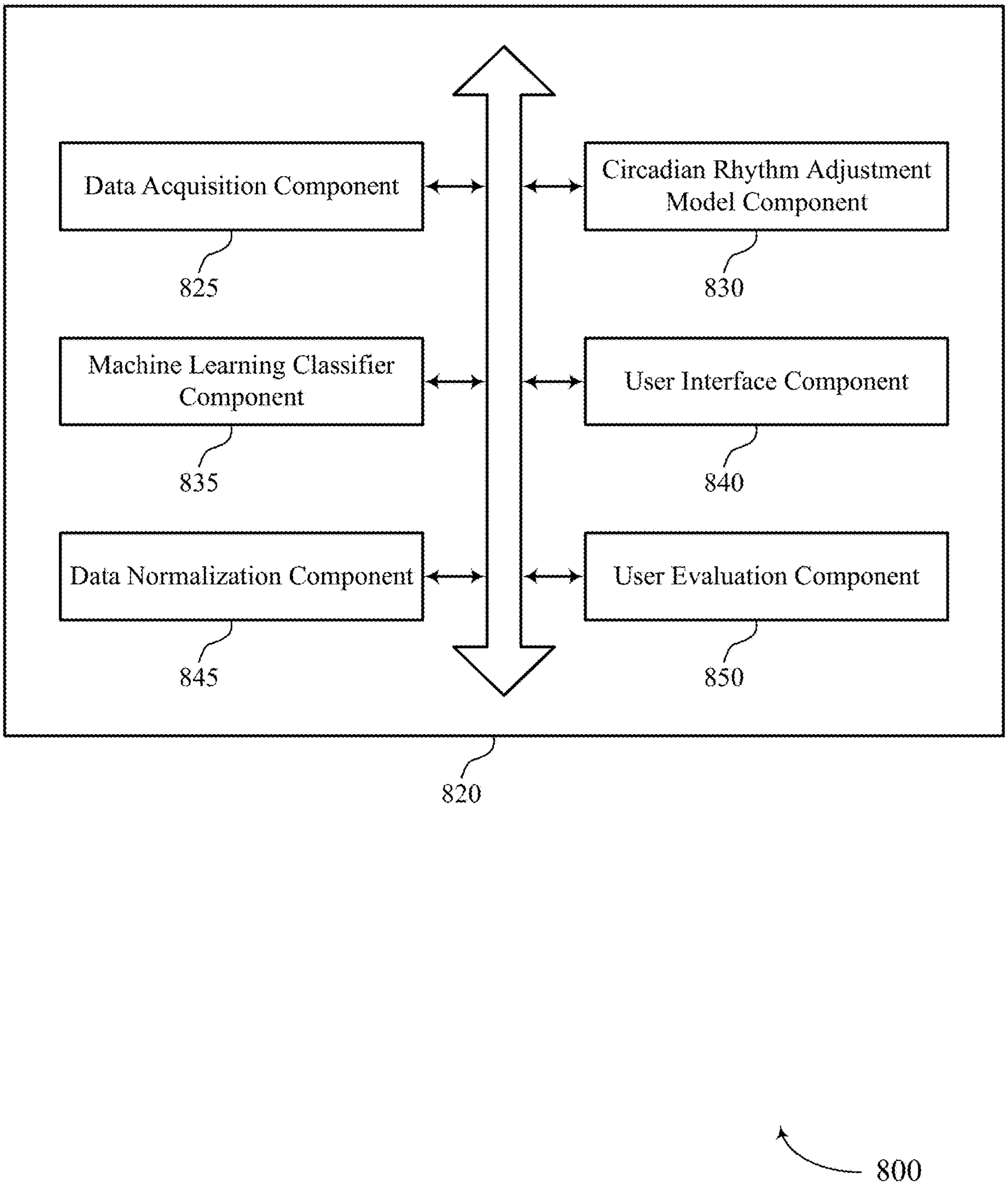
FIG. 8 shows a block diagram of a wearable application that supports sleep staging algorithms with circadian rhythm adjustment in accordance with aspects of the present disclosure.

FIG. 8 shows a block diagram 800 of a wearable application 820 that supports sleep staging algorithms with circadian rhythm adjustment in accordance with aspects of the present disclosure. The wearable application 820 may be an example of aspects of a wearable application or a wearable application 720, or both, as described herein. The wearable application 820, or various components thereof, may be an example of means for performing various aspects of sleep staging algorithms as described herein. For example, the wearable application 820 may include a data acquisition component 825, a circadian rhythm adjustment model component 830, a machine learning classifier component 835, a user interface component 840, a data normalization component 845, a user evaluation component 850, or any combination thereof. Each of these components may communicate, directly or indirectly, with one another (e.g., via one or more buses).

The wearable application 820 may support techniques for detecting sleep stages in accordance with examples as disclosed herein. The data acquisition component 825 may be configured as or otherwise support a means for receiving physiological data associated with a user from a wearable device, the physiological data collected via the wearable device throughout a time interval. The circadian rhythm adjustment model component 830 may be configured as or otherwise support a means for identifying a circadian rhythm adjustment model configured to weight the physiological data based at least in part on a circadian rhythm associated with the user. The machine learning classifier component 835 may be configured as or otherwise support a means for inputting the physiological data and the circadian rhythm adjustment model into a machine learning classifier. In some examples, the machine learning classifier component 835 may be configured as or otherwise support a means for classifying the physiological data, using the machine learning classifier, into at least one sleep stage of a plurality of sleep stages for at least a portion of the time interval, wherein the classifying is based at least in part on the circadian rhythm adjustment model. The user interface component 840 may be configured as or otherwise support a means for causing a GUI of a user device to display an indication of the at least one sleep stage of the plurality of sleep stages based at least in part on classifying the physiological data.

In some examples, the data acquisition component 825 may be configured as or otherwise support a means for receiving additional physiological data associated with the user from the wearable device, the additional physiological data collected via the wearable device throughout at least an additional time interval prior to the time interval. In some examples, the circadian rhythm adjustment model component 830 may be configured as or otherwise support a means for generating the circadian rhythm adjustment model for the user based at least in part on the additional physiological data.

In some examples, the circadian rhythm adjustment model component 830 may be configured as or otherwise support a means for identifying a baseline circadian rhythm adjustment model, wherein generating the circadian rhythm adjustment model for the user comprises selectively modifying the baseline circadian rhythm adjustment model based at least in part on the additional physiological data.

In some examples, the circadian rhythm adjustment model comprises a circadian drive component, a homeostatic sleep pressure component, an elapsed sleep duration component, or any combination thereof. In some examples, the circadian drive component comprises a sinusoidal function, the homeostatic sleep pressure component comprises an exponential decay function, and the elapsed sleep duration component comprises a linear function.

In some examples, to support classifying the physiological data, the machine learning classifier component 835 may be configured as or otherwise support a means for selectively weighting a plurality of probability metrics associated with a plurality of subsets of the time interval based at least in part on the circadian rhythm adjustment model, wherein each probability metric comprises a probability that the corresponding subset of the time interval is associated with a respective sleep stage of the plurality of sleep stages.

In some examples, the data acquisition component 825 may be configured as or otherwise support a means for identifying, based at least in part on the physiological data, a time duration from a most recent sleep period for the user. In some examples, the machine learning classifier component 835 may be configured as or otherwise support a means for inputting the time duration into the machine learning classifier, wherein classifying the physiological data is based at least in part on the time duration.

In some examples, to support classifying the physiological data, the machine learning classifier component 835 may be configured as or otherwise support a means for selectively weighting, using the circadian rhythm adjustment model, a plurality of probability metrics associated with a plurality of subsets of the time interval based at least in part on the time duration, wherein each probability metric comprises a probability that the corresponding subset of the time interval is associated with a respective sleep stage of the plurality of sleep stages.

In some examples, to support classifying the physiological data, the machine learning classifier component 835 may be configured as or otherwise support a means for classifying the physiological data collected throughout the time interval into a plurality of sleep intervals within the time interval. In some examples, to support classifying the physiological data, the machine learning classifier component 835 may be configured as or otherwise support a means for classifying each sleep interval of the plurality of sleep intervals into at least one of an awake sleep stage, a light sleep stage, a rapid eye movement sleep stage, or a deep sleep stage.

In some examples, the user interface component 840 may be configured as or otherwise support a means for causing the GUI of the user device to display one or more sleep intervals of the plurality of sleep intervals. In some examples, the user interface component 840 may be configured as or otherwise support a means for causing the GUI of the user device to display a classified sleep stage corresponding to each sleep interval of the one or more sleep intervals.

In some examples, the data normalization component 845 may be configured as or otherwise support a means for performing one or more normalization procedures on the physiological data, wherein inputting the physiological data into the machine learning classifier comprises inputting the normalized physiological data into the machine learning classifier.

In some examples, the machine learning classifier component 835 may be configured as or otherwise support a means for identifying, using the machine learning classifier, a plurality of features associated with the physiological data, wherein classifying the physiological data is based at least in part on identifying the plurality of features.

In some examples, the plurality of features comprise a rate of change of the physiological data, a pattern between two or more parameters of the physiological data, a maximum data value of the physiological data, a minimum data value of the physiological data, an average data value of the physiological data, a median data value of the physiological data, a comparison of a data value of the physiological data to a baseline data value for the user, or any combination thereof.

In some examples, the user interface component 840 may be configured as or otherwise support a means for causing the GUI of the user device to display one or more features of the plurality of features.

In some examples, the user evaluation component 850 may be configured as or otherwise support a means for identifying a bed time associated with the user, a wake time associated with the user, or both, based at least in part on the circadian rhythm adjustment model, classifying the physiological data, or both. In some examples, the user interface component 840 may be configured as or otherwise support a means for causing the GUI of the user device to display the bed time, the wake time, or both.

In some examples, the physiological data comprises temperature data, accelerometer data, heart rate data, heart rate variability data, blood oxygen level data, or any combination thereof. In some examples, the wearable device collects the physiological data from the user based on arterial blood flow within a finger of the user. In some examples, the wearable device collects the physiological data from the user using one or more red LEDs and one or more green LEDs.

Figure 9:
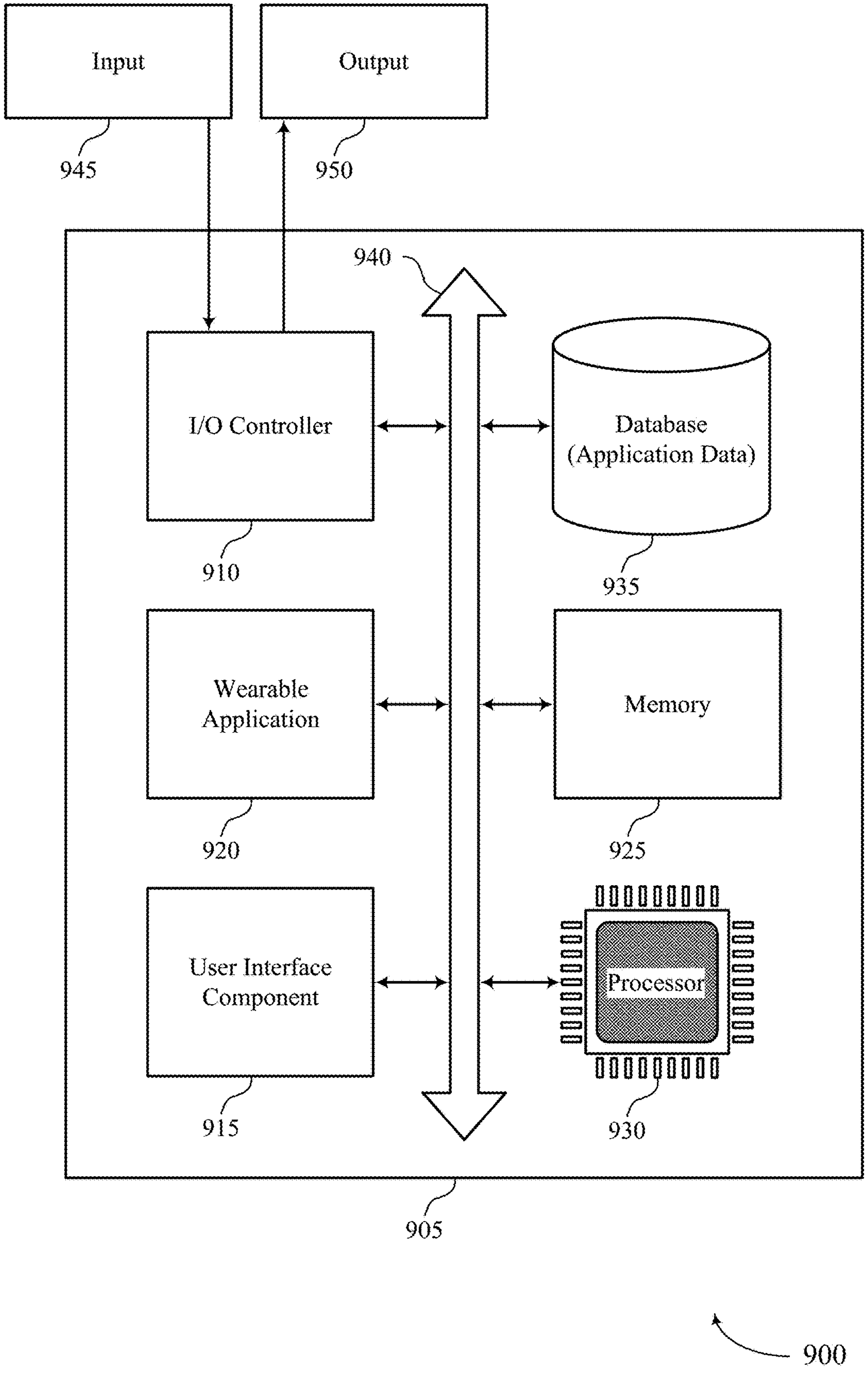
FIG. 9 shows a diagram of a system including a device that supports sleep staging algorithms with circadian rhythm adjustment in accordance with aspects of the present disclosure.

FIG. 9 shows a diagram of a system 900 including a device 905 that supports sleep staging algorithms with circadian rhythm adjustment in accordance with aspects of the present disclosure. The device 905 may be an example of or include the components of a device 705 as described herein. The device 905 may include components for bi-directional data communications including components for transmitting and receiving communications, such as a wearable application 920, an I/O controller 910, a user interface component 915, a memory 925, a processor 930, and a database 935. These components may be in electronic communication or otherwise coupled (e.g., operatively, communicatively, functionally, electronically, electrically) via one or more buses (e.g., a bus 940).

The I/O controller 910 may manage input signals 945 and output signals 950 for the device 905. The I/O controller may include an example of the communication module of the user device shown and described in FIG. 2. In this regard, the input signals 945 and output signals 950 may illustrate signaling exchanged between the user device and the ring, and the user device and the servers, as illustrated in FIG. 2. The I/O controller 910 may also manage peripherals not integrated into the device 905. In some cases, the I/O controller 910 may represent a physical connection or port to an external peripheral. In some cases, the I/O controller 910 may utilize an operating system such as iOS®, ANDROID®, MS-DOS®, MS-WINDOWS®, OS/2®, UNIX®, LINUX®, or another known operating system. In other cases, the I/O controller 910 may represent or interact with a wearable device (e.g., ring), modem, a keyboard, a mouse, a touchscreen, or a similar device. In some cases, the I/O controller 910 may be implemented as part of a processor 930. In some examples, a user may interact with the device 905 via the I/O controller 910 or via hardware components controlled by the I/O controller 910.

The user interface component 915 may manage data storage and processing in a database 935. In some cases, a user may interact with the user interface component 915. In other cases, the user interface component 915 may operate automatically without user interaction. The database 935 may be an example of a single database, a distributed database, multiple distributed databases, a data store, a data lake, or an emergency backup database.

Memory 925 may include RAM and ROM. The memory 925 may store computer-readable, computer-executable software including instructions that, when executed, cause the processor 930 to perform various functions described herein. In some cases, the memory 925 may contain, among other things, a basic I/O system (BIOS) that may control basic hardware or software operation such as the interaction with peripheral components or devices.

The processor 930 may include an intelligent hardware device, (e.g., a general-purpose processor, a digital signal processor (DSP), a central processing unit (CPU), a microcontroller, an application-specific integrated circuit (ASIC), a field-programmable gate array (FPGA), a programmable logic device, a discrete gate or transistor logic component, a discrete hardware component, or any combination thereof). In some cases, the processor 930 may be configured to operate a memory array using a memory controller. In other cases, a memory controller may be integrated into the processor 930. The processor 930 may be configured to execute computer-readable instructions stored in a memory 925 to perform various functions (e.g., functions or tasks supporting a method and system for sleep staging algorithms).

The wearable application 920 may support techniques for detecting sleep stages in accordance with examples as disclosed herein. For example, the wearable application 920 may be configured as or otherwise support a means for receiving physiological data associated with a user from a wearable device, the physiological data collected via the wearable device throughout a time interval. The wearable application 920 may be configured as or otherwise support a means for identifying a circadian rhythm adjustment model configured to weight the physiological data based at least in part on a circadian rhythm associated with the user. The wearable application 920 may be configured as or otherwise support a means for inputting the physiological data and the circadian rhythm adjustment model into a machine learning classifier. The wearable application 920 may be configured as or otherwise support a means for classifying the physiological data, using the machine learning classifier, into at least one sleep stage of a plurality of sleep stages for at least a portion of the time interval, wherein the classifying is based at least in part on the circadian rhythm adjustment model. The wearable application 920 may be configured as or otherwise support a means for causing a GUI of a user device to display an indication of the at least one sleep stage of the plurality of sleep stages based at least in part on classifying the physiological data.

By including or configuring the wearable application 920 in accordance with examples as described herein, the device 905 may support techniques for improved sleep staging algorithms. In particular, techniques descried herein may enable more accurate and efficient identification of multiple sleep stages. By providing a user with a more comprehensive evaluation of their sleep stages and sleeping patterns, techniques described herein may enable the user to effectively adjust their sleep patterns, and may improve the sleep quality and overall health for the user.

Figure 10:
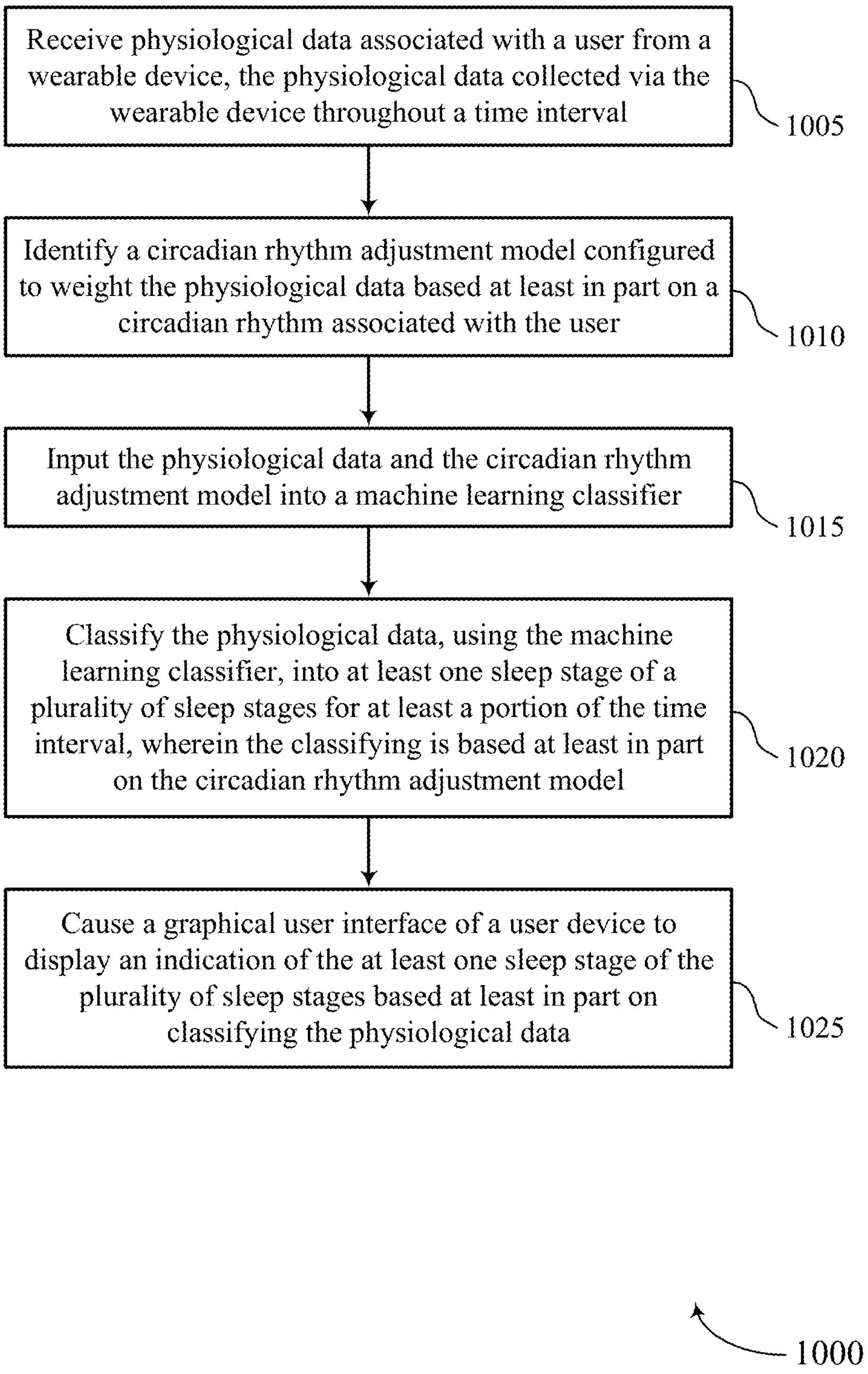
FIGS. 10 through 12 show flowcharts illustrating methods that support sleep staging algorithms with circadian rhythm adjustment in accordance with aspects of the present disclosure.

FIG. 10 shows a flowchart illustrating a method 1000 that supports sleep staging algorithms with circadian rhythm adjustment in accordance with aspects of the present disclosure. The operations of the method 1000 may be implemented by a User device or its components as described herein. For example, the operations of the method 1000 may be performed by a User device as described with reference to FIGS. 1 through 9. In some examples, a User device may execute a set of instructions to control the functional elements of the User device to perform the described functions. Additionally, or alternatively, the User device may perform aspects of the described functions using special-purpose hardware.

At 1005, the method may include receiving physiological data associated with a user from a wearable device, the physiological data collected via the wearable device throughout a time interval. The operations of 1005 may be performed in accordance with examples as disclosed herein. In some examples, aspects of the operations of 1005 may be performed by a data acquisition component 825 as described with reference to FIG. 8.

At 1010, the method may include identifying a circadian rhythm adjustment model configured to weight the physiological data based at least in part on a circadian rhythm associated with the user. The operations of 1010 may be performed in accordance with examples as disclosed herein. In some examples, aspects of the operations of 1010 may be performed by a circadian rhythm adjustment model component 830 as described with reference to FIG. 8.

At 1015, the method may include inputting the physiological data and the circadian rhythm adjustment model into a machine learning classifier. The operations of 1015 may be performed in accordance with examples as disclosed herein. In some examples, aspects of the operations of 1015 may be performed by a machine learning classifier component 835 as described with reference to FIG. 8.

At 1020, the method may include classifying the physiological data, using the machine learning classifier, into at least one sleep stage of a plurality of sleep stages for at least a portion of the time interval, wherein the classifying is based at least in part on the circadian rhythm adjustment model. The operations of 1020 may be performed in accordance with examples as disclosed herein. In some examples, aspects of the operations of 1020 may be performed by a machine learning classifier component 835 as described with reference to FIG. 8.

At 1025, the method may include causing a GUI of a user device to display an indication of the at least one sleep stage of the plurality of sleep stages based at least in part on classifying the physiological data. The operations of 1025 may be performed in accordance with examples as disclosed herein. In some examples, aspects of the operations of 1025 may be performed by a user interface component 840 as described with reference to FIG. 8.

Figure 11:
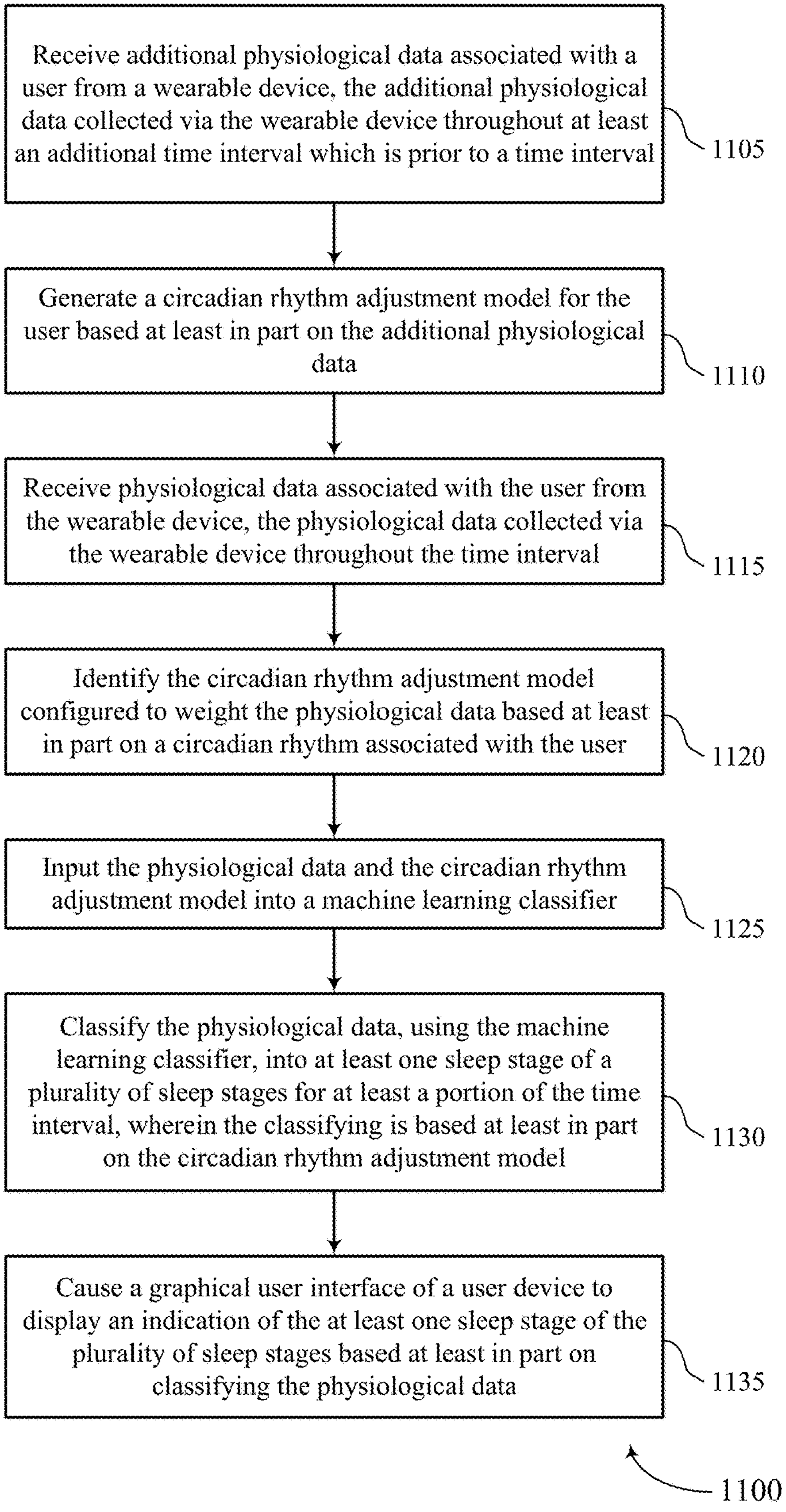

FIG. 11 shows a flowchart illustrating a method 1100 that supports sleep staging algorithms with circadian rhythm adjustment in accordance with aspects of the present disclosure. The operations of the method 1100 may be implemented by a User device or its components as described herein. For example, the operations of the method 1100 may be performed by a User device as described with reference to FIGS. 1 through 9. In some examples, a User device may execute a set of instructions to control the functional elements of the User device to perform the described functions. Additionally, or alternatively, the User device may perform aspects of the described functions using special-purpose hardware.

At 1105, the method may include receiving additional physiological data associated with a user from a wearable device, the additional physiological data collected via the wearable device throughout at least an additional time interval prior to a time interval. The operations of 1105 may be performed in accordance with examples as disclosed herein. In some examples, aspects of the operations of 1105 may be performed by a data acquisition component 825 as described with reference to FIG. 8.

At 1110, the method may include generating a circadian rhythm adjustment model for the user based at least in part on the additional physiological data. The operations of 1110 may be performed in accordance with examples as disclosed herein. In some examples, aspects of the operations of 1110 may be performed by a circadian rhythm adjustment model component 830 as described with reference to FIG. 8.

At 1115, the method may include receiving physiological data associated with the user from the wearable device, the physiological data collected via the wearable device throughout the time interval. The operations of 1115 may be performed in accordance with examples as disclosed herein. In some examples, aspects of the operations of 1115 may be performed by a data acquisition component 825 as described with reference to FIG. 8.

At 1120, the method may include identifying the circadian rhythm adjustment model configured to weight the physiological data based at least in part on a circadian rhythm associated with the user. The operations of 1120 may be performed in accordance with examples as disclosed herein. In some examples, aspects of the operations of 1120 may be performed by a circadian rhythm adjustment model component 830 as described with reference to FIG. 8.

At 1125, the method may include inputting the physiological data and the circadian rhythm adjustment model into a machine learning classifier. The operations of 1125 may be performed in accordance with examples as disclosed herein. In some examples, aspects of the operations of 1125 may be performed by a machine learning classifier component 835 as described with reference to FIG. 8.

At 1130, the method may include classifying the physiological data, using the machine learning classifier, into at least one sleep stage of a plurality of sleep stages for at least a portion of the time interval, wherein the classifying is based at least in part on the circadian rhythm adjustment model. The operations of 1130 may be performed in accordance with examples as disclosed herein. In some examples, aspects of the operations of 1130 may be performed by a machine learning classifier component 835 as described with reference to FIG. 8.

At 1135, the method may include causing a GUI of a user device to display an indication of the at least one sleep stage of the plurality of sleep stages based at least in part on classifying the physiological data. The operations of 1135 may be performed in accordance with examples as disclosed herein. In some examples, aspects of the operations of 1135 may be performed by a user interface component 840 as described with reference to FIG. 8.

Figure 12:
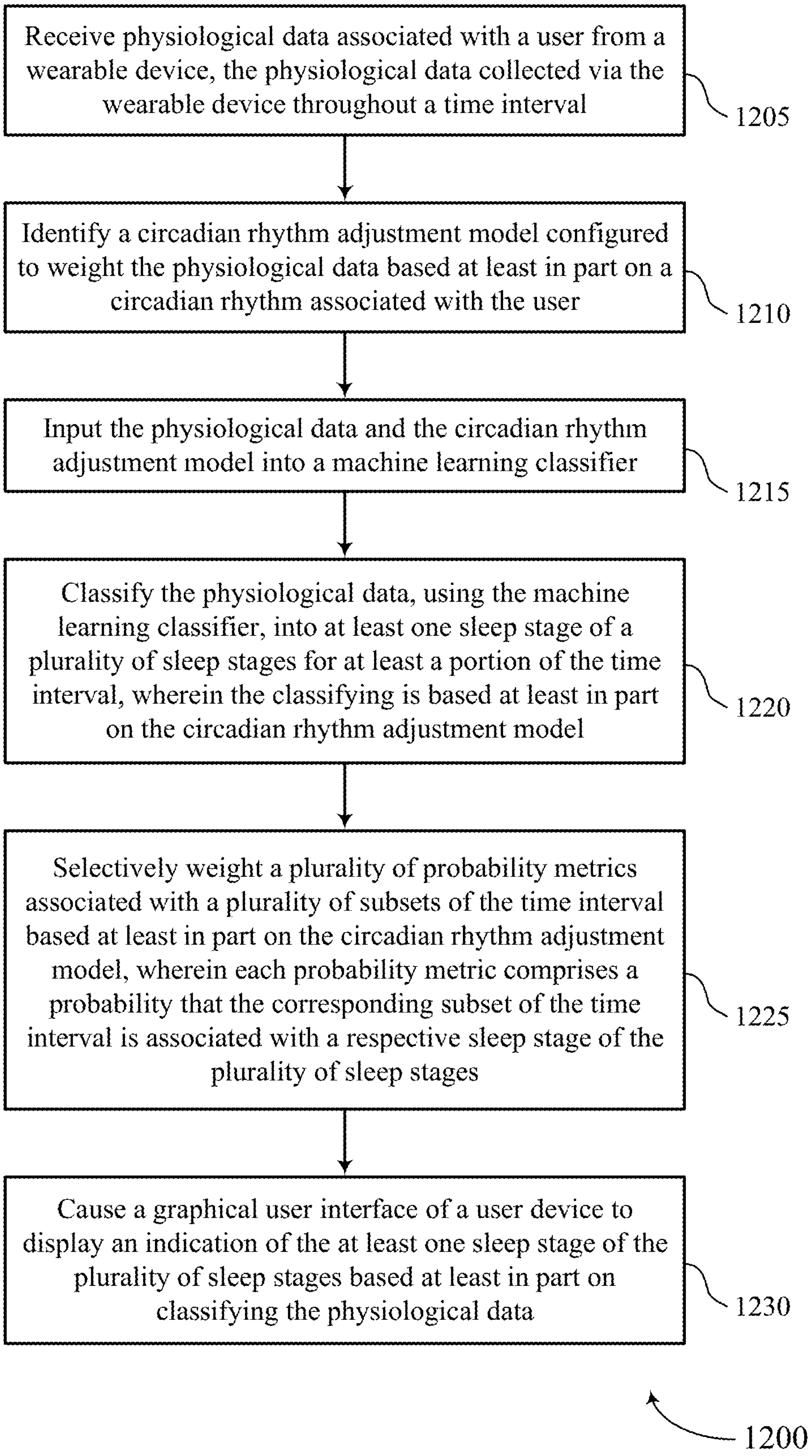

FIG. 12 shows a flowchart illustrating a method 1200 that supports sleep staging algorithms with circadian rhythm adjustment in accordance with aspects of the present disclosure. The operations of the method 1200 may be implemented by a User device or its components as described herein. For example, the operations of the method 1200 may be performed by a User device as described with reference to FIGS. 1 through 9. In some examples, a User device may execute a set of instructions to control the functional elements of the User device to perform the described functions. Additionally, or alternatively, the User device may perform aspects of the described functions using special-purpose hardware.

At 1205, the method may include receiving physiological data associated with a user from a wearable device, the physiological data collected via the wearable device throughout a time interval. The operations of 1205 may be performed in accordance with examples as disclosed herein. In some examples, aspects of the operations of 1205 may be performed by a data acquisition component 825 as described with reference to FIG. 8.

At 1210, the method may include identifying a circadian rhythm adjustment model configured to weight the physiological data based at least in part on a circadian rhythm associated with the user. The operations of 1210 may be performed in accordance with examples as disclosed herein. In some examples, aspects of the operations of 1210 may be performed by a circadian rhythm adjustment model component 830 as described with reference to FIG. 8.

At 1215, the method may include inputting the physiological data and the circadian rhythm adjustment model into a machine learning classifier. The operations of 1215 may be performed in accordance with examples as disclosed herein. In some examples, aspects of the operations of 1215 may be performed by a machine learning classifier component 835 as described with reference to FIG. 8.

At 1220, the method may include classifying the physiological data, using the machine learning classifier, into at least one sleep stage of a plurality of sleep stages for at least a portion of the time interval, wherein the classifying is based at least in part on the circadian rhythm adjustment model. The operations of 1220 may be performed in accordance with examples as disclosed herein. In some examples, aspects of the operations of 1220 may be performed by a machine learning classifier component 835 as described with reference to FIG. 8.

At 1225, the method may include selectively weighting a plurality of probability metrics associated with a plurality of subsets of the time interval based at least in part on the circadian rhythm adjustment model, wherein each probability metric comprises a probability that the corresponding subset of the time interval is associated with a respective sleep stage of the plurality of sleep stages. The operations of 1225 may be performed in accordance with examples as disclosed herein. In some examples, aspects of the operations of 1225 may be performed by a machine learning classifier component 835 as described with reference to FIG. 8.

At 1230, the method may include causing a GUI of a user device to display an indication of the at least one sleep stage of the plurality of sleep stages based at least in part on classifying the physiological data. The operations of 1230 may be performed in accordance with examples as disclosed herein. In some examples, aspects of the operations of 1230 may be performed by a user interface component 840 as described with reference to FIG. 8.

A method for automatically detecting sleep stages is described. The method may include receiving physiological data associated with a user from a wearable device, the physiological data collected via the wearable device throughout a time interval, identifying a circadian rhythm adjustment model configured to weight the physiological data based at least in part on a circadian rhythm associated with the user, inputting the physiological data and the circadian rhythm adjustment model into a machine learning classifier, classifying the physiological data, using the machine learning classifier, into at least one sleep stage of a plurality of sleep stages for at least a portion of the time interval, wherein the classifying is based at least in part on the circadian rhythm adjustment model, and causing a GUI of a user device to display an indication of the at least one sleep stage of the plurality of sleep stages based at least in part on classifying the physiological data.

An apparatus for automatically detecting sleep stages is described. The apparatus may include a processor, memory coupled with the processor, and instructions stored in the memory. The instructions may be executable by the processor to cause the apparatus to receive physiological data associated with a user from a wearable device, the physiological data collected via the wearable device throughout a time interval, identify a circadian rhythm adjustment model configured to weight the physiological data based at least in part on a circadian rhythm associated with the user, input the physiological data and the circadian rhythm adjustment model into a machine learning classifier, classify the physiological data, using the machine learning classifier, into at least one sleep stage of a plurality of sleep stages for at least a portion of the time interval, wherein the classifying is based at least in part on the circadian rhythm adjustment model, and cause a GUI of a user device to display an indication of the at least one sleep stage of the plurality of sleep stages based at least in part on classifying the physiological data.

Another apparatus for automatically detecting sleep stages is described. The apparatus may include means for receiving physiological data associated with a user from a wearable device, the physiological data collected via the wearable device throughout a time interval, means for identifying a circadian rhythm adjustment model configured to weight the physiological data based at least in part on a circadian rhythm associated with the user, means for inputting the physiological data and the circadian rhythm adjustment model into a machine learning classifier, means for classifying the physiological data, using the machine learning classifier, into at least one sleep stage of a plurality of sleep stages for at least a portion of the time interval, wherein the classifying is based at least in part on the circadian rhythm adjustment model, and means for causing a GUI of a user device to display an indication of the at least one sleep stage of the plurality of sleep stages based at least in part on classifying the physiological data.

A non-transitory computer-readable medium storing code for automatically detecting sleep stages is described. The code may include instructions executable by a processor to receive physiological data associated with a user from a wearable device, the physiological data collected via the wearable device throughout a time interval, identify a circadian rhythm adjustment model configured to weight the physiological data based at least in part on a circadian rhythm associated with the user, input the physiological data and the circadian rhythm adjustment model into a machine learning classifier, classify the physiological data, using the machine learning classifier, into at least one sleep stage of a plurality of sleep stages for at least a portion of the time interval, wherein the classifying is based at least in part on the circadian rhythm adjustment model, and cause a GUI of a user device to display an indication of the at least one sleep stage of the plurality of sleep stages based at least in part on classifying the physiological data.

Some examples of the method, apparatuses, and non-transitory computer-readable medium described herein may further include operations, features, means, or instructions for receiving additional physiological data associated with the user from the wearable device, the additional physiological data collected via the wearable device throughout at least an additional time interval prior to the time interval and generating the circadian rhythm adjustment model for the user based at least in part on the additional physiological data.

Some examples of the method, apparatuses, and non-transitory computer-readable medium described herein may further include operations, features, means, or instructions for identifying a baseline circadian rhythm adjustment model, wherein generating the circadian rhythm adjustment model for the user comprises selectively modifying the baseline circadian rhythm adjustment model based at least in part on the additional physiological data.

In some examples of the method, apparatuses, and non-transitory computer-readable medium described herein, the circadian rhythm adjustment model comprises a circadian drive component, a homeostatic sleep pressure component, an elapsed sleep duration component, or any combination thereof.

In some examples of the method, apparatuses, and non-transitory computer-readable medium described herein, the circadian drive component comprises a sinusoidal function, the homeostatic sleep pressure component comprises an exponential decay function, and the elapsed sleep duration component comprises a linear function.

In some examples of the method, apparatuses, and non-transitory computer-readable medium described herein, classifying the physiological data may include operations, features, means, or instructions for selectively weighting a plurality of probability metrics associated with a plurality of subsets of the time interval based at least in part on the circadian rhythm adjustment model, wherein each probability metric comprises a probability that a corresponding subset of the time interval may be associated with a respective sleep stage of the plurality of sleep stages.

Some examples of the method, apparatuses, and non-transitory computer-readable medium described herein may further include operations, features, means, or instructions for identifying, based at least in part on the physiological data, a time duration from a most recent sleep period for the user and inputting the time duration into the machine learning classifier, wherein classifying the physiological data may be based at least in part on the time duration.

In some examples of the method, apparatuses, and non-transitory computer-readable medium described herein, classifying the physiological data may include operations, features, means, or instructions for selectively weighting, using the circadian rhythm adjustment model, a plurality of probability metrics associated with a plurality of subsets of the time interval based at least in part on the time duration, wherein each probability metric comprises a probability that a corresponding subset of the time interval may be associated with a respective sleep stage of the plurality of sleep stages.

In some examples of the method, apparatuses, and non-transitory computer-readable medium described herein, classifying the physiological data may include operations, features, means, or instructions for classifying the physiological data collected throughout the time interval into a plurality of sleep intervals within the time interval and classifying each sleep interval of the plurality of sleep intervals into at least one of an awake sleep stage, a light sleep stage, a REM sleep stage, or a deep sleep stage.

Some examples of the method, apparatuses, and non-transitory computer-readable medium described herein may further include operations, features, means, or instructions for causing the GUI of the user device to display one or more sleep intervals of the plurality of sleep intervals and causing the GUI of the user device to display a classified sleep stage corresponding to each sleep interval of the one or more sleep intervals.

Some examples of the method, apparatuses, and non-transitory computer-readable medium described herein may further include operations, features, means, or instructions for performing one or more normalization procedures on the physiological data, wherein inputting the physiological data into the machine learning classifier comprises inputting the normalized physiological data into the machine learning classifier.

Some examples of the method, apparatuses, and non-transitory computer-readable medium described herein may further include operations, features, means, or instructions for identifying, using the machine learning classifier, a plurality of features associated with the physiological data, wherein classifying the physiological data may be based at least in part on identifying the plurality of features.

In some examples of the method, apparatuses, and non-transitory computer-readable medium described herein, the plurality of features comprise a rate of change of the physiological data, a pattern between two or more parameters of the physiological data, a maximum data value of the physiological data, a minimum data value of the physiological data, an average data value of the physiological data, a median data value of the physiological data, a comparison of a data value of the physiological data to a baseline data value for the user, or any combination thereof.

Some examples of the method, apparatuses, and non-transitory computer-readable medium described herein may further include operations, features, means, or instructions for causing the GUI of the user device to display one or more features of the plurality of features.

Some examples of the method, apparatuses, and non-transitory computer-readable medium described herein may further include operations, features, means, or instructions for identifying a bed time associated with the user, a wake time associated with the user, or both, based at least in part on the circadian rhythm adjustment model, classifying the physiological data, or both and causing the GUI of the user device to display the bed time, the wake time, or both.

In some examples of the method, apparatuses, and non-transitory computer-readable medium described herein, the physiological data comprises temperature data, accelerometer data, heart rate data, HRV data, blood oxygen level data, or any combination thereof.

In some examples of the method, apparatuses, and non-transitory computer-readable medium described herein, the wearable device collects the physiological data from the user based on arterial blood flow within a finger of the user.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A system for automatically classifying time intervals into one of a plurality of sleep stages, comprising:

a wearable device comprising one or more sensors, wherein the one or more sensors include at least one optical transmitter and at least one optical receiver, the at least one optical transmitter configured to transmit light to illuminate a region of a user, the at least one optical receiver configured to receive light transmitted from the at least one optical transmitter and generate a photoplethysmogram (PPG) signal indicative of an amount of the light received, and the PPG signal indicative of perfusion of blood in the illuminated region;

a user device communicatively coupled with the wearable device; and one or more processors communicatively coupled with the wearable device and the user device, the one or more processors configured to:

sample the PPG signal to determine a pulse waveform of the user;

determine, via the one or more sensors of the wearable device, physiological data associated with the user, wherein the physiological data is based in part on the pulse waveform of the user, wherein the physiological data comprises temperature data, heart rate data, and heart rate variability data, wherein the physiological data is continuously determined throughout a first sleep period, and wherein the first sleep period comprises a plurality of time intervals;

modify a baseline circadian rhythm adjustment model in accordance with the physiological data to generate a modified circadian rhythm adjustment model corresponding to the user, wherein the modified circadian rhythm adjustment model comprises a circadian drive component, a homeostatic sleep pressure component, and an elapsed sleep duration component, wherein a temporal starting point for the circadian drive component, the homeostatic sleep pressure component, and the elapsed sleep duration component corresponds to a bedtime of the user;

determine the bedtime of the user associated with the first sleep period based at least in part on the physiological data;

identify one or more sensor-independent circadian features representative of a circadian rhythm associated with the user based on the modified circadian rhythm adjustment model, wherein the one or more sensor-independent circadian features are representative of physiological changes in sleep stage distribution of the user throughout the first sleep period;

assign a first weight to a first probability metric for a first time interval of the plurality of time intervals based at least in part on the modified circadian rhythm adjustment model and a first elapsed time between the bedtime of the user and the first time interval, wherein the first probability metric is associated with a probability of the first time interval corresponding to a deep sleep stage of the plurality of sleep stages;

assign a second weight to a second probability metric for a second time interval of the plurality of time intervals based at least in part on the modified circadian rhythm adjustment model and a second elapsed time between the bedtime of the user and the second time interval, wherein the second probability metric is associated with a probability of the second time interval corresponding to the deep sleep stage, wherein the first weight is greater than the second weight based at least in part on the first time interval occurring earlier in the first sleep period than the second time interval;

classify, using a machine learning model trained to include the one or more sensor-independent circadian features modeled by the modified circadian rhythm adjustment model, the first time interval as the deep sleep stage based at least in part on the first weight of the first probability metric; and cause a graphical user interface of the user device to display an indication of the plurality of time intervals of the first sleep period including at least the deep sleep stage classified using the machine learning model.

2. The system of claim 1, wherein the one or more processors are further configured to:

classify, using the machine learning model trained to include the one or more sensor-independent circadian features modeled by the modified circadian rhythm adjustment model, the second time interval as a rapid eye movement sleep stage based at least in part on the second weight of the second probability metric; and cause the graphical user interface of the user device to display the rapid eye movement sleep stage classified using the machine learning model.

3. The system of claim 1, wherein the one or more processors are further configured to:

identify that the heart rate data is higher relative to a heart rate baseline within the first elapsed time between the bedtime of the user and the first time interval; and identify that a sleep pressure of the user, indicated via the homeostatic sleep pressure component of the modified circadian rhythm adjustment model, is higher relative to a sleep pressure baseline within the first elapsed time between the bedtime of the user and the first time interval, wherein assigning the first weight to the first probability metric is based at least in part on identifying the heart rate data is higher relative to the heart rate baseline and identifying that the sleep pressure is higher relative to the sleep pressure baseline.

4. The system of claim 1, wherein to assign the first weight to the first probability metric and assign the second weight to the second probability metric, the one or more processors are configured to:

apply a plurality of weighting functions that comprise the circadian drive component, the homeostatic sleep pressure component, and the elapsed sleep duration component.

5. The system of claim 1, wherein the circadian drive component comprises a sinusoidal function, the homeostatic sleep pressure component comprises an exponential decay function that indicates a decay of sleep pressure associated with the user throughout the first sleep period and the elapsed sleep duration component comprises a linear function that indicates a time duration from the bedtime of the user.

6. The system of claim 1, wherein assigning the first weight to the first probability metric and assigning the second weight to the second probability metric is based at least in part on a phase of the circadian rhythm associated with the user.

7. The system of claim 1, wherein the one or more processors are further configured to:

identify, based at least in part on the physiological data, a time duration from a most recent sleep period for the user, wherein the time duration indicates an amount of sleep pressure that the user is experiencing; and input the time duration into the machine learning model, wherein classifying the first time interval as the deep sleep stage is based at least in part on the time duration.

8. The system of claim 7, wherein the one or more processors are further configured to:

adjust the homeostatic sleep pressure component of the modified circadian rhythm adjustment model based at least in part on identifying the time duration from the most recent sleep period.

9. The system of claim 1, wherein the one or more processors are further configured to:

classify each time interval of the plurality of time intervals into at least one of an awake sleep stage, a light sleep stage, a rapid eye movement sleep stage, or the deep sleep stage.

10. The system of claim 9, wherein the one or more processors are further configured to:

cause the graphical user interface of the user device to display a classified sleep stage corresponding to each time interval of the plurality of time intervals.

11. The system of claim 1, wherein the one or more processors are further configured to:

normalize the physiological data on a per-night basis to account for differences in absolute values between different users;

and input the normalized physiological data into the machine learning model.

12. The system of claim 1, wherein the one or more processors are further configured to:

identify, using the machine learning model, a plurality of features associated with the physiological data, wherein classifying the first sleep period as the deep sleep stage is based at least in part on identifying the plurality of features; and cause the graphical user interface of the user device to display one or more features of the plurality of features.

13. The system of claim 12, wherein the plurality of features comprise a rate of change of the physiological data, a pattern between two or more parameters of the physiological data, a maximum data value of the physiological data, a minimum data value of the physiological data, an average data value of the physiological data, a median data value of the physiological data, a comparison of a data value of the physiological data to a baseline data value for the user, or any combination thereof.

14. The system of claim 9, wherein the one or more processors are further configured to:

generate one or more recommendations based on each time interval classified; and cause the graphical user interface of the user device to display the one or more recommendations, wherein the one or more recommendations include at least one of a recommended bedtime or a recommended wake time for improving at least one of sleep quality or overall health of the user.

15. The system of claim 1, wherein the one or more processors are further configured to:

identify a wake time associated with the user based at least in part on classifying the first sleep period as the deep sleep stage; and cause the graphical user interface of the user device to display the bedtime, the wake time, or both.

16. The system of claim 1, wherein the physiological data further comprises accelerometer data, blood oxygen level data, or both.

17. The system of claim 1, wherein the body part comprises a finger of the user.

18. The system of claim 1, wherein the at least one optical transmitter comprises one or more red light emitting diodes and one or more green light emitting diodes.

19. An apparatus for automatically classifying time intervals into one of a plurality of sleep stages, comprising:

one or more processors;

memory coupled with the one or more processors; and instructions stored in the memory and executable by the one or more processors to cause the apparatus to:

sample, via one or more sensors of a wearable device, a photoplethysmogram (PPG) signal to determine a pulse waveform of the user, wherein the one or more sensors include at least one optical transmitter and at least one optical receiver, the at least one optical transmitter configured to transmit light to illuminate a region of a user, the at least one optical receiver configured to receive light transmitted from the at least one optical transmitter and generate the PPG signal indicative of an amount of the light received, and the PPG signal indicative of perfusion of blood in the illuminated region;

determine, via the one or more sensors, physiological data associated with a user, wherein the physiological data is based in part on the pulse waveform of the user, wherein the physiological data comprises temperature data, heart rate data, and heart rate variability data, wherein the physiological data is continuously determined throughout a first sleep period, and wherein the first sleep period comprises a plurality of time intervals;

modify a baseline circadian rhythm adjustment model in accordance with the physiological data to generate a modified circadian rhythm adjustment model corresponding to the user, wherein the modified circadian rhythm adjustment model comprises a circadian drive component, a homeostatic sleep pressure component, and an elapsed sleep duration component, wherein a temporal starting point for the circadian drive component, the homeostatic sleep pressure component, and the elapsed sleep duration component corresponds to a bedtime of the user;

determine the bedtime of the user associated with the first sleep period based at least in part on the physiological data;

identify one or more sensor-independent circadian features representative of a circadian rhythm associated with the user based on the modified circadian rhythm adjustment model, wherein the one or more sensor-independent circadian features are representative of physiological changes in sleep stage distribution of the user throughout the first sleep period;

assign a first weight to a first probability metric for a first time interval of the plurality of time intervals based at least in part on the modified circadian rhythm adjustment model and a first elapsed time between the bedtime of the user and the first time interval, wherein the first probability metric is associated with a probability of the first time interval corresponding to a deep sleep stage of the plurality of sleep stages;

assign a second weight to a second probability metric for a second time interval of the plurality of time intervals based at least in part on the modified circadian rhythm adjustment model and a second elapsed time between the bedtime of the user and the second time interval, wherein the second probability metric is associated with a probability of the second time interval corresponding to the deep sleep stage, wherein the first weight is greater than the second weight based at least in part on the first time interval occurring earlier in the first sleep period than the second time interval;

classify, using a machine learning model trained to include the one or more sensor-independent circadian features modeled by the modified circadian rhythm adjustment model, the first time interval as the deep sleep stage based at least in part on the first weight of the first probability metric; and cause a graphical user interface of a user device to display an indication of the plurality of time intervals of the first sleep period including at least the deep sleep stage classified using the machine learning model.

20. The apparatus of claim 19, wherein the instructions are further executable by the one or more processors to cause the apparatus to:

classify, using the machine learning model trained to include the one or more sensor-independent circadian features modeled by the modified circadian rhythm adjustment model, the second time interval as a rapid eye movement sleep stage based at least in part on the second weight of the second probability metric; and cause the graphical user interface of the user device to display the rapid eye movement sleep stage classified using the machine learning model.

* * * * *